(12) United States Patent
Brooks et al.

(10) Patent No.: US 7,662,783 B2
(45) Date of Patent: Feb. 16, 2010

(54) CLK-PEPTIDE AND SLK-PEPTIDE

(75) Inventors: Peter C. Brooks, Carmel, NY (US); Jennifer Roth, North Babylon, NY (US); Abebe Akalu, Forest Hills, NY (US)

(73) Assignee: New York University, New York, NY (US)

( * ) Notice: Subject to any disclaimer, the term of this patent is extended or adjusted under 35 U.S.C. 154(b) by 200 days.

(21) Appl. No.: 11/251,442

(22) Filed: Oct. 14, 2005

(65) Prior Publication Data

US 2007/0259817 A1 Nov. 8, 2007

Related U.S. Application Data

(63) Continuation-in-part of application No. 10/782,728, filed on Feb. 18, 2004.

(60) Provisional application No. 60/449,250, filed on Feb. 20, 2003.

(51) Int. Cl.
*A61K 38/10* (2006.01)
(52) U.S. Cl. ..................... 514/15; 435/173.1
(58) Field of Classification Search ................ None
See application file for complete search history.

(56) References Cited

U.S. PATENT DOCUMENTS

| | | | |
|---|---|---|---|
| 5,092,885 A | 3/1992 | Yamada et al. | |
| 5,112,946 A | 5/1992 | Maione | |
| 5,192,744 A | 3/1993 | Bouck et al. | |
| 5,202,352 A | 4/1993 | Okada et al. | |
| 6,071,520 A | 6/2000 | Noteborn et al. | |
| 7,122,635 B2 * | 10/2006 | Brooks et al. | 530/387.1 |
| 2004/0224896 A1 | 11/2004 | Brooks | |

FOREIGN PATENT DOCUMENTS

| | | |
|---|---|---|
| WO | WO-00-40597 A1 | 7/2000 |
| WO | WO-00-59532 A1 | 10/2000 |
| WO | WO-2004-073649 A2 | 2/2004 |

OTHER PUBLICATIONS

National Cancer Institute, "Radiation Therapy", www.cancer.gov.*
Akalu, A. et al., "Inhibition of angiogenesis and tumor metastasis by targeting a matrix immobilized cryptic extracellular matrix epitope in laminin," Cancer Res. 67(9):4353-4363 (2007).
Gonzalez, A. et al., "Complex interactions between the laminin alpha 4 subunit and integrins egulate endothelial cell behavior in vitro and angiogenesis in vivo," PNAS USA 99(25):16075-16080 (2002).
Kikkawa, Y. et al., "Isolation and characterization of laminin-10/11 secreted by human lung carcinoma cells. Laminin-10/11 mediates cell adhesion through integrin alpha3 beta1," J. Biol. Chem. (online), Am. Soc. Biochem. Mol. Biol., 273 (25):15854-15859 (1998).
Kurkinen, M. et al., "In vitro synthesis of laminin and entactin polypeptides," J. Biol. Chem. 258(l0):6543-6548 (1983).
EP04758409.9 Supp EP Search Report dated Jul. 19, 2007.
Amstutz, et al., "In vitro display technologies: novel developments and applications," Curr. Op. Biotech. 12:400-405 (2001).
Auerbach, R. et al., "Angiogenesis Assays: A Critical Overview," Clin. Chem. 49(1):32-40 (2003).
Auerbach, R. et al., "Angiogenesis assays: Problems and pitfalls," Cancer Metastasis Rev. 19:167-172 (2000).
Battegay, E.J., "Angiogenesis: mechanistic insights, neovascular diseases, and therapeutic prospects," J. Mol. Med. 73:333-346 (1995).
Blood, C.H. et al., "Tumor interactions with the vasculature: angiogenesis and tumor metastasis," Biochim. Biophys. Acta. 1032:89-118 (1990).
Brooks, P. et al., "Integrin $\alpha_v\beta_3$ Antagonists Promote Tumor Regression by Inducing Apoptosis of Angiogenic Blood Vessels," Cell 79:1157-1162 (1994).
Brooks, P. et al., "Disruption of Angiogenesis by PEX, a Noncatalytic Metalloproteinase Fragment with Integrin Binding Activity," Cell 92:391-400 (1998).
Brooks, P. et al., "Antiintegrin $\alpha_v\beta_3$ blocks human breast cancer growth and angiogenesis in human skin," J. Clin. Invest. 96:1815-1822 (1995).
Burgess, W.H. et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," J. Cell. Biol. 111:2129-2138 (1990).
Engel, J., "Versatile cololagens in invertebrates," Science 277:1785-1786 (1997).
Fischer, C., "Principles and Therapeutic Implications of Angiogenesis, Vasculogenesis and Arteriogenesis," HEP 176(11):157-212 (2006).
Gordon et al., "The contribution of collagenous proteins to tissue-specific matrix assemblies," Curr. Op. Cell Biol. 2:833-838 (1990).
Green et al., PNAS USA 100:1010-1015 (2003).
Guo et al., "In vitro evolution of amphioxus insulin-like peptide to mammalian insulin," Biochem. 41:10603-10607 (2002).
Guo, H. et al., "Protein tolerance to random amino acid change," PNAS USA 101(25):9205-9210 (2004).
Hangai et al., "Matrix metalloproteinase-9-dependent exposure of a cryptic migratory control site in collagen is required before retinal angiogenesis," Am. J. Pathology 161(4):1429-1437 (2002).
Heeley, R.P., Endocr. Res. 28:217-229 (2002).
Ingham et al., "Type 1 collagen contains at least 14 cryptic fibronectin binding sires of similiar affinity," Arch. Biochem. Biophys. 407:217-223 (2002).

(Continued)

*Primary Examiner*—Christopher R. Tate
*Assistant Examiner*—Roy Teller
(74) *Attorney, Agent, or Firm*—Wilson Sonsini Goodrich & Rosati

(57) ABSTRACT

The invention describes methods for inhibiting angiogenesis in a tissue by administering an antagonist that specifically binds to a proteolyzed or denatured collagen type-IV with substantially greater affinity than to the native triple helical form of collagen type-IV. Methods utilizing such antagonists for therapeutic treatment of tumor growth, tumor metastasis or of restenosis also are described, as are methods to use such antagonists as diagnostic markers of angiogenesis in normal or diseased tissues both in vivo and ex vivo. The invention further describes methods for treating tumors using said antagonists in combination with radiation therapy and therapies comprising the antagonists and radiation treatment.

9 Claims, 26 Drawing Sheets

OTHER PUBLICATIONS

Jo, N. et al., "Inhibitory effect of an antibody to cryptic collagen type IV epitopes on choroidal neovascularization," Mol. Vision 12:1243-1249 (2006).

Jones, D.T., "Critically assessing the state-of-the-art in protein structure prediction," Pharmacogenomics J. 1:126-134 (2001).

Kim, J. et al., "Inhibition of Angiogenesis and Angiogenesis-dependent Tumor Growth by the Cryptic Kringle Fragments of Human Apolipoprotein(a)*," J. Biol. Chem. 278:29000-29008 (2003).

Kim, S. et al., "Regulation of Angiogenesis In Vivo by Ligation of Integrin α5β1 with the Central Cell-Binding Domain of Fibronectin," Am. J. Path. 156:1345-1362 (2000).

Kurschat, P., "Mechanisms of Metastasis," Clin. Exp. Dermatol. 25:482-489 (2000).

Lazar, E. et al., "Transforming Growth Factor α: Mutation of Aspartic Acid 47 and Leucine 48 Results in Different Biological Activities," Mol. Cell. Biol. 8:1247-1252 (1988).

Liljeblad et al., "Analaysis of agalacto-IgG in rheumatoid arthritis using surface plasmon resonance," Glycoconjugate J. 17:323-329 (2000).

Liotta, L. A. et al., "Cancer Metastasis and Angiogenesis: An Imbalance of Positive and Negative Regulation," Cell 65:327-336 (1991).

Qin, X. et al., "Structure-Function Analysis of the Human Insulin-like Growth Factor Binding Protein-4*," JBC 273(36):23509-23516 (1998).

Roskelley, C.D. et al., "A hierarchy of ECM-mediated signalling regulates tissue-specific gene expression," Curr. Op. Cell Biol. 7:736-747 (1995).

Skolnick, J. et al., "From genes to protein structure and function: novel applications of computational approaches in the genomic era," Trends Biotech. 18:34-39 (2000).

Staton, C.A. et al., "Current methods for assaying angiogenesis in vitro and in vivo," Intl J. Exp. Path. 85:233-248 (2004).

Steffensen et al., "Human fibronectin and MMp-2 collagen binding domains competer for collagen binding site and modify cellular activation of MMP-2," Matrix Biol. 21:399-414 (2002).

Stephanopoulos, G., "Metabolic engineering by genome shuffling," Nature Biotech. 20(7):666-668 (2002).

Tani et al., "In vitro selection of fibronectin gain-of-function mutations," Biochem. J. 365:287-294 (2002).

Tosatto, S.C.E. et al., "Large-Scale Prediction of Protein Structure and Function from Sequence," Curr. Pharma. Des. 12:2067-2086 (2006).

Varner et al., Cell Adh. Commun. 3:367-374 (1995).

Weidner, N. et al., "Tumor Angiogenesis: A New Significant and Independent Prognostic Indicator in Early-Stage Breast Carcinoma," J. Natl. Cancer Inst. 84:1875-1887 (1992).

Weidner, N. et al., "Tumor Angiogensis and Metastasis-Correlation in Invasive Breast Carcinoma," N. Engl. J. Med. 324:1-7 (1991).

Wyckoff, J., "A Critical Step in Metastasis: In Vivo Analysis of Intravasation at the Primary Tumor," Cancer Res. 60:2504-2511 (2000).

Xu et al., "Generatio of monoclonal antibodies to cryptic site within collagen type IV is required for angiogenesis and tumor growth in vivo," J. Cell Biol. 154(5):1069-1079 (2001).

Xu et al., "Proteolytic exposure of a cryptic site within collagen type IV is required for angiogenesis and tumor growth in vivo," J. Cell Biol. 154(5):1069-1079 (2001).

Zhao et al., "Directed evolution of enzymes and pathways for industrial biocatalysis," Curr. Op. Biotech. 13:104-110 (2002).

Ponce, M. L. et al., "An angiogenic laminin site and its antagonist bind through the αvβ3 and α5β1 integrins," The FASEB J. 15:1389-1397 (2001).

Yepes, M. et al., "Neuroserpin reduces cerebral infarct volume and protects neurons from ischemia-induced apoptosis," Blood 96:569-576 (2000).

* cited by examiner

```
                          SEQUENCE LISTING

<160> NUMBER OF SEQ ID NOS: 5

<210> SEQ ID NO 1
<211> LENGTH: 10
<212> TYPE: PRT
<213> ORGANISM: Artificial
<220> FEATURE:
<223> OTHER INFORMATION: denatured collagen type-IV selective antagonist

<400> SEQUENCE: 1

Leu Lys Gln Asn Gly Gly Asn Phe Ser Leu
1               5                   10

<210> SEQ ID NO 2
<211> LENGTH: 12
<212> TYPE: PRT
<213> ORGANISM: Artificial
<220> FEATURE:
<223> OTHER INFORMATION: denatured collagen type-IV selective antagonist

<400> SEQUENCE: 2

Cys Leu Lys Gln Asn Gly Gly Asn Phe Ser Leu Gly
1               5                   10

<210> SEQ ID NO 3
<211> LENGTH: 12
<212> TYPE: PRT
<213> ORGANISM: Artificial
<220> FEATURE:
<223> OTHER INFORMATION: denatured collagen type-IV selective antagonist

<400> SEQUENCE: 3

Ser Leu Lys Gln Asn Gly Gly Asn Phe Ser Leu Cys
1               5                   10

<210> SEQ ID NO 4
<211> LENGTH: 18
<212> TYPE: PRT
<213> ORGANISM: Artificial
<220> FEATURE:
<223> OTHER INFORMATION: denatured collagen type-IV selective antagonist

<400> SEQUENCE: 4

Lys Gly Gly Cys Leu Lys Gln Asn Gly Gly Asn Phe Ser Leu Gly Gly
1               5                   10                  15

Lys Ala

<210> SEQ ID NO 5
<211> LENGTH: 13
<212> TYPE: PRT
<213> ORGANISM: Artificial
<220> FEATURE:
<223> OTHER INFORMATION: control peptide

<400> SEQUENCE: 5

Cys Thr Trp Pro Arg His His Thr Thr Asp Ala Leu Leu
1               5                   10
```

CLK-PEPTIDE AND SLK-PEPTIDE

CLAIM OF PRIORITY

This application is a continuation-in-part of prior U.S. application Ser. No. 10/782,728, filed Feb. 18, 2004. U.S. application Ser. No. 10/782,728 claims priority under 35 U.S.C. §119(e) to U.S. application Ser. No. 60/449,250 filed on Feb. 20, 2003. The contents of U.S. application Ser. Nos. 10/782,728 and 60/449,250 are hereby incorporated by reference in their entirety.

STATEMENT OF FEDERALLY-SPONSORED RESEARCH

The present invention was made with Government support under a contract 2RO1CA91645 awarded by the National Institutes of Health. The United States Government may have certain rights to the this invention pursuant to the grant.

FIELD OF THE INVENTION

This invention relates generally to the field of medicine, and more specifically to methods and compositions for inhibiting or detecting angiogenesis, tumor growth and metastases using active agents comprising selective antagonists of denatured collagen type-IV.

BACKGROUND

Tumor growth and metastasis impact a large number of people each year. It is estimated that over 600,000 new cases of cancer will be diagnosed in the United States per year (Varner, J., et al., Cell Adh. Commun. 1995; 3:367-374).

Metastasis, the spread of malignant tumor cells from the primary tumor mass to distant sites involves a complex series of interconnected events. (Liotta, et al., Cell 1991; 64:327-336; Wyckoff, et al., Cancer Res. 2000; 60:2504-2511; Kurschat, et al., Clinc. Exp. Dermatol. 2000; 25:482-489.) The metastatic cascade is initiated by a series of genetic alterations leading to changes in cell-cell interaction, which allow tumor cells to dissociate from the primary tumor mass. The dissociated cells locally invade and migrate through proteolytically modified extracellular matrix (ECM). The dissociated cells gain access to the circulatory system. To establish a metastatic deposit, the circulating tumor cells must evade host immune defenses, arrest in the microvasculature, and extravasate out of the circulation. The tumor cells then invade the ECM at the new site, proliferate, induce angiogenesis, and continue to grow.

Therapies designed to block angiogenesis may significantly effect the growth of solid tumors and metastases. Blocking tumor neovascularization significantly inhibits tumor growth in various animal models, and human clinical data is beginning to support this contention as well (Varner, J., et al., Cell Adh. Commun. 1995; 3:367-374). These and other studies suggest that the growth of solid tumors requires new blood vessel growth for continued expansion of the tumors beyond a minimal size (Varner et al., 1995; Blood, C. H., et. al., Biochim. Biophys. Acta. 1990; 1032:89-118; Weidner, N. et al. J Natl. Cancer Inst. 1992; 84:1875-1887; Weidner, N. et al., N. Engl. J Med. 1991; 324:1-7; Brooks, P. C. et al. J Clin. Invest. 1995; 96:1815-1822; Brooks, P. C. et al., Cell 1994; 79:1157-1164; Brooks, P. C. et al. Cell 1996; 85:683-693; Brooks, P. C. et al., Cell 1998; 92:391-400). Inhibition of angiogenesis is, therefore, a promising treatment for cancer and metastatic disease.

Angiogenesis is the physiological process by which new blood vessels develop from pre-existing vessels (Varner et al., 1995; Blood et al., 1990; Weidner et al., 1992). This complex process requires cooperation of a variety of molecules including growth factors, cell adhesion receptors, matrix degrading enzymes and extracellular matrix components (Varner et al., 1995; Blood et al., 1990; Weidner et al., 1992).

Inhibition of angiogenesis may also be useful in treating other diseases that are characterized by unregulated blood vessel development including, for example, ocular diseases (e.g., macular degeneration and diabetic retinopathy) and inflammatory diseases (e.g., arthritis and psoriasis) (Varner et al., 1995).

Many investigators have focused their anti-angiogenic approaches towards growth factors and cytokines that initiate angiogenesis (Varner et al., 1995; Blood et al., 1990; Weidner et al., 1992; Weidner et al., 1991; Brooks et al., 1995; Brooks et al., 1994; Brooks et al., 1997). There are, however, a large number of growth factors and cytokines that have the capacity to stimulate angiogenesis. The therapeutic benefit of blocking a single cytokine, therefore, may have only limited benefit due to this redundancy. Little attention has been directed to other anti-angiogenic targets.

Recent studies have suggested that angiogenesis requires proteolytic remodeling of the extracellular matrix (ECM) surrounding blood vessels in order to provide a microenvironment conducive to new blood vessel development (Varner et al. (1995); Blood et al. (1990); Weidner et al. (1992); Weidner et al. (1991); Brooks et al. (1995); Brooks et al. (1994); Brooks et al. (1997)). The extracellular matrix protein collagen makes up over 25% of the total protein mass in animals and the majority of protein within the ECM.

Inhibition of angiogenesis would be a useful therapy for restricting tumor growth and metastases. Inhibition of angiogenesis may be effected by (1) inhibition of release of "angiogenic molecules" such as, for example, bFGF (basic fibroblast growth factor), (2) neutralization of angiogenic molecules, (e.g., anti-bFGF antibodies), and (3) inhibition of endothelial cell response to angiogenic stimuli. (Folkman et al., Cancer Biology, 3:89-96 (1992)). Several potential endothelial cell response inhibitors have been described that might be used to inhibit angiogenesis, e.g., collagenase inhibitors, basement membrane turnover inhibitors, angiostatic steroids, fungal-derived angiogenesis inhibitors, platelet factor 4, thrombospondin, arthritis drugs such as D-penicillamine and gold thiomalate, vitamin D3 analogs, and alpha-interferon. Additional proposed inhibitors of angiogenesis have also been described in the literature. (Blood, et al. (1990); Moses et al. (1990) Science 248:1408-1410; Ingber, et al. (1988) Lab. Invest., 59:44-5 1; and U.S. Pat. Nos. 5,092,885; 5,112, 946; 5,192,744; and 5,202,352.)

Collagen is an extracellular matrix protein containing a [Gly-Xaa-Xaa]n sequence motif. Collagen types are well known in the art (see, e.g., Olsen, B. R. (1995) Curr. Op. Cell. Biol. 5:720-727; Kucharz, E. J. The Collagens: Biochemistry and Pathophysiology. Springer-Verlag, Berlin, 1992; Kunn, K. in Structure and Function of Collagen Types, eds. R. Mayne and R. E. Burgeson, Academic Press, Orlando). Collagen is a fibrous multi-chain triple helical protein that exists in numerous forms (Olsen, B. R. (1995) Curr. Opin. Cell Biol 7, 720-727; Van der Rest, M., et al. (1991) FASEB 5, 2814-2823). At least 18 genetically distinct types of collagen have been identified, many of which have distinct tissue distributions and functions (Olsen (1995); Van der Rest, et al. (1991)). Collagen type-I is the most abundant collagen in the extracellular matrix. Collagen type-I, collagen type-III, collagen type-IV and collagen type-V have been shown to be associated with all pre-existing blood vessels in vivo.

The mature collagen molecule is composed of two α1 chains and one α2 chain twisted into a triple helix. Collagens type-I and type-IV, for example, are composed of major chains designated α1(I) and α2(I) and α1(IV) and α2(IV), respectively. In vivo, collagen is normally found in the mature triple helical form.

Denaturation of the native three dimensional structure of mature triple helical collagen may expose cryptic regulatory regions that control angiogenesis. Disruption by antibodies of cellular interactions with denatured collagen type-IV blocks tumor growth and angiogenesis (Xu, J., et al. (2001) J. Cell Biol. Vol. 154:1069-1079; Hangia, et al. (2002) Am. J. Pathol. Vol. 161:1429-1437). Brooks et al. (PCT WO 00/40597) discloses antibodies that bind to cryptic regions within various denatured collagen types.

It has now been surprisingly discovered that peptide antagonists selective for denatured collagen type-IV inhibit angiogenesis and tumor growth. Peptide antagonists that specifically bind to denatured collagen type-IV provide the basis for powerful new compounds for treating cancer, inflammatory diseases and other angiogenesis-associated diseases.

SUMMARY OF THE INVENTION

The invention provides a method for inhibiting angiogenesis, tumor growth and metastasis in the tissue of a mammal by administering to the mammal an active agent comprising an angiogenesis-inhibiting amount of a selective antagonist of denatured collagen type-IV.

The invention also provides a method for inhibiting tumor growth and metastasis in the tissue of a mammal by administering to the mammal an active agent comprising a tumor cell adhesion-inhibiting amount of a selective antagonist of denatured collagen type-IV.

The present invention also provides peptide antagonists that specifically bind to denatured collagen type-IV and can be used to inhibit angiogenesis, tumor growth and metastasis in mammals. More specifically, the invention provides biologically active agents comprising denatured collagen type-IV selective antagonists that inhibit angiogenesis, tumor growth and metastasis. The binding affinity of the peptide antagonists of the present invention to denatured collagen type-IV is substantially greater than the binding affinity of the antagonists to native forms of collagen type-IV.

The denatured collagen type-IV selective antagonists for use in the present invention have a core amino acid sequence L-K-Q-N-G-G-N-F-S-L.

A preferred denatured collagen type-IV selective antagonist for use in the present invention is a peptide having the amino acid sequence NH2-C-L-K-Q-N-G-G-N-F-S-L-G-COOH (CLK-peptide).

Another preferred denatured collagen type-IV selective antagonist for use in the present invention is a peptide having the amino acid sequence NH2-S-L-K-Q-N-G-G-N-F-S-L-C-COOH (SLK peptide).

Another preferred denatured collagen type-IV selective antagonist for use in the present invention is a peptide having the amino acid sequence NH2-K-G-G-C-L-K-Q-N-G-G-N-F-S-L-G-G-K-A-COOH (KGGCLK peptide).

In another embodiment of the invention, the denatured collagen type-IV selective antagonist is conjugated to a cytotoxic or cytostatic agent.

In another aspect, the invention provides methods for detecting angiogenesis in a mammalian tissue by exposing the tissue to a detectably labeled denatured collagen type-IV selective antagonist.

In a still further embodiment, the invention includes a method for detecting tumorous tissue, metastases, tumor invasion, bacterial invasion, arthritis, inflammation or any other disease or condition that is characterized or associated with denaturation of collagen type-IV in a mammalian tissue by exposing the tissue to be tested to a detectably labeled denatured collagen type-IV selective antagonist.

The present invention provides methods for treating a tumor in a patient, inhibiting tumor cell adhesion, inhibiting metastasis, inhibiting tumor cell proliferation, or inhibiting tumor growth comprising administering an effective amount of a denatured collagen type-IV selective peptide antagonist comprising a core amino acid sequence referenced as SEQ ID NO: 1 in combination with radiation therapy. Peptide antagonists useful in the methods of the invention include SEQ ID NO: 2, SEQ ID NO: 3, and SEQ ID NO: 4, as well as substitutions of these sequences, and sequences including additional flanking sequences, so long as the peptides have substantially the same functional activity as the core sequence.

Tumors contemplated for treatment in the methods of the invention include solid tumors is selected from the group consisting of: glioblastoma; neuroblastoma; Kaposi's sarcoma; and tumors of the skin, melanoma, lung, pancreas, liver, breast, colon, larynx, pharynx, ovary, uterus, cervix, endometrius, prostate, stomach, intestine, colorectal, head, neck, testicle, lymph node, marrow, bone or joint, kidney, bladder, and sweat gland.

In embodiments of the invention, the radiation therapy used comprises ionizing radiation. The invention contemplates the use of radiation therapy comprising gamma rays, X-rays, electrons, neutrons, electromagnetic radiation, particulate radiation, electron beams (beta particles), proton beams, neutron beams, alpha particles or negative pi mesons. Radiation therapies used in embodiments of the invention include radiation therapy comprising electromagnetic radiation or particulate radiation. In further embodiments, a total of at least about: 1 Gy, 5 Gy, 10 Gy, 20 Gy, or 40 Gy of radiation is administered to the patient.

The present invention also encompasses a method of increasing the effectiveness of solid tumor radiation treatment comprising contacting an effective amount of an antagonist comprising the amino acid sequence referenced as SEQ ID NO: 1, SEQ ID NO: 2, SEQ ID NO: 3, SEQ ID NO: 4 or functional substitutions, with a solid tumor and subjecting the tumor to radiation, wherein the effectiveness is substantially increased when compared to radiation treatment alone.

In embodiments of the invention, the methods of increasing the effectiveness of solid tumor radiation treatment are used in vivo, for example, in a mammal or a cancer patient, or in vitro.

The invention additionally includes a method of sensitizing a neoplastic cell to radiation treatment, comprising administering to said neoplastic cell a sensitizing amount of an antagonist comprising the amino acid sequence referenced as SEQ ID NO: 1, SEQ ID NO: 2, SEQ ID NO: 3, SEQ ID NO: 4 or functional substitutions and exposing said cell to a dose of radiation, wherein the sensitivity is substantially increased when compared to radiation treatment alone.

In further embodiments the methods of sensitizing a neoplastic cell to radiation treatment are used in vivo, for example, in a mammal or a cancer patient, or in vitro.

The present invention provides combination therapies for treatment of tumors comprising an effective amount of an antagonist comprising the amino acid sequence referenced as SEQ ID NO: 1, SEQ ID NO: 2, SEQ ID NO: 3, SEQ ID NO: 4 or functional substitutions in combination with radiation therapy. In embodiments, tumors treated using these therapies are selected from the group consisting of: glioblastoma; neuroblastoma; Kaposi's sarcoma; and tumors of the skin, melanoma, lung, pancreas, liver, breast, colon, larynx, pharynx, ovary, uterus, cervix, endometrius, prostate, stomach, intestine, colorectal, head, neck, testicle, lymph node, marrow, bone or joint, kidney, bladder, and sweat gland.

The radiation therapy used in the combination therapies of the invention comprise ionizing radiation. The invention contemplates the use of radiation therapy comprising gamma rays, X-rays, electrons, neutrons, electromagnetic radiation, particulate radiation, electron beams (beta particles), proton beams, neutron beams, alpha particles or negative pi mesons. Radiation therapies used in embodiments of the invention include radiation therapy comprising electromagnetic radiation or particulate radiation. In further embodiments, a total of at least about: 1 Gy, 5 Gy, 10 Gy, 20 Gy, or 40 Gy of radiation is administered to the patient.

DETAILED DESCRIPTION OF THE INVENTION

Figure 1:
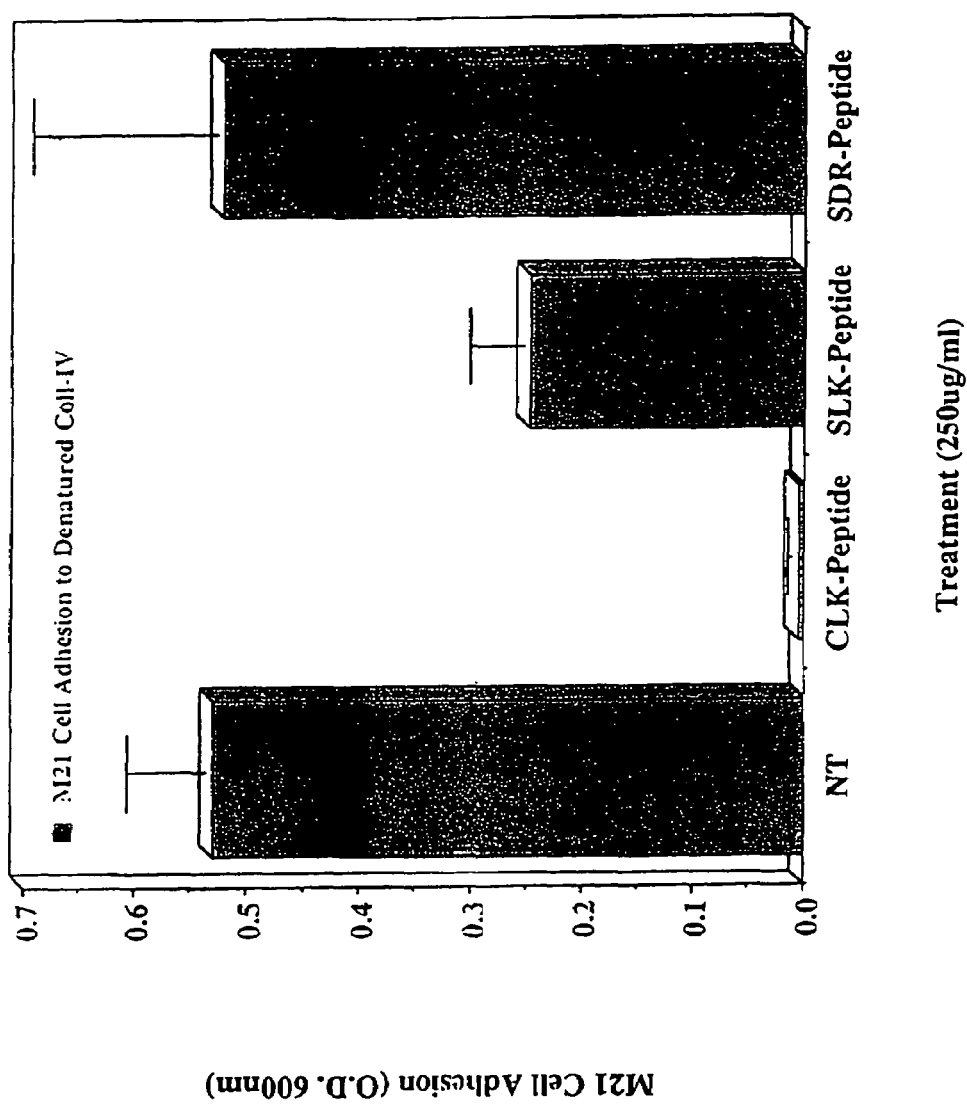
FIG. 1 is a chart which illustrates M21 human melanoma cell adhesion to untreated denatured type-IV collagen (NT), CLK-peptide treated denatured collagen type-IV, SLK-peptide treated denatured collagen type-IV, and SDR-peptide treated denatured collagen type-IV.

The present invention provides compositions and methods for inhibiting. angiogenesis, tumor growth, metastasis, bacterial invasion, arthritis, inflammation or any other disease or condition that is characterized or associated with denaturation of collagen type-IV in mammals and for detecting angiogenesis, tumor growth, metastasis, bacterial invasion, arthritis, inflammation or any other disease or condition that is characterized or associated with denaturation of collagen type-IV in mammalian tissue through the use of denatured collagen type-IV selective antagonists. Peptides having the amino acid core L-K-Q-N-G-G-N-F-S-L selectively bind denatured collagen type-IV.

The methods of the present invention provide biologically active agents that inhibit the formation of new blood vessels required to establish and sustain cancer cells. Additionally, the present invention provides methods and compositions that directly inhibit tumor growth, metastasis, inflammation, and other diseases or conditions associated with cellular interactions with denatured collagen type-IV. The active agents of the present invention selectively bind to denatured collagen type-IV thereby preventing angiogenesis, tumor growth, metastasis, arthritis, inflammatory diseases and other diseases or conditions associated with cellular interactions with such collagen.

Definitions

As used herein, the term "angiogenesis" includes a variety of processes involving neovascularization of a tissue including "sprouting", vasculogenesis, or vessel enlargement, all of which angiogenesis processes involve disruption of extracellular matrix collagen in blood vessels. Angiogenesis that takes place during traumatic wound healing, corpus luteum formation and embryogenesis is a part of normal physiology. The majority of angiogenesis cases, however, are associated with disease processes.

As used herein, "antagonist" refers to a compound that inhibits a naturally occurring biological activity.

As used herein, a "cryptic epitope" within a collagen is a sequence that is not exposed for recognition within a native collagen, but is capable of being recognized by an antagonist of a denatured collagen. Peptide sequences that are not solvent exposed or are only partially solvent exposed in the native structure are potential cryptic epitopes. The sequence of cryptic epitopes can be identified by determining the specificity of an antagonist. Candidate cryptic epitopes also can be identified, for example, by examining the three dimensional structure of a native triple helical collagen.

As used herein "native collagen" refers to collagen that is predominantly in its triple helical form.

As used herein "denatured collagen" refers to collagen that is no longer predominantly in its native triple helical form. The denatured collagen can be denatured full-length collagen or a fragment of collagen. A fragment of collagen can be any collagen sequence shorter than a full length collagen sequence. For fragments of collagen with substantial native structure, denaturation can be effected as for a native full-length collagen. Fragments also can be of a size such that they do not possess significant native structure or possess regions without significant native triple helical form. The term "denatured collagen" encompasses "proteolyzed collagen". "Proteolyzed collagen" refers to a collagen that has been structurally altered through the action of a proteolytic enzyme.

As used herein, a "denatured collagen type-IV selective antagonist" is a substance that has a substantially greater binding affinity to denatured collagen type-IV than to native collagen type-IV.

As used herein, an "epitope" is that amino acid sequence or sequences that are recognized by an antagonist of the invention. An epitope can be a linear peptide sequence or can be composed of noncontiguous amino acid sequences. An antagonist can recognize one or more sequences, therefore an epitope can define more than one distinct amino acid sequence target. The epitopes recognized by an antagonist can be determined by peptide mapping and sequence analysis techniques well known to one of skill in the art.

The term "peptide" as used herein refers to a series of two or more covalently linked amino acids. A linear, cyclic, or branched peptide can be used in practicing the invention.

The term "core amino acid sequence" as used herein refers to a sequence of amino acids that can begin at the N-terminus of a peptide, can be an internal sequence in a peptide, or can end at the C-terminus of a peptide.

As used herein, the term "peptido-mimetic" is used to refer to compounds that mimic the activity of a peptide. Peptidomimetics are non-peptides but may comprise amino acids linked by non-peptide bonds. In a peptido-mimetic, the three dimensional structure of a peptide that specifically interacts with the three dimensional structure of a cryptic epitope is duplicated by a molecule that is not a peptide.

"Neovascularization" as used herein means the development of new blood vessels. Neovascularization may refer to the process of angiogenesis and/or to the result of angiogenesis, which is new blood vessel formation.

As defined herein, a "patient" is any mammal in which treatment of angiogenic diseases, tumor growth or metastasis is desirable. Preferred patients include agricultural or domestic mammals; for example, a pig, a cow, a horse, a goat, a sheep, a mule, a donkey, a dog, a cat, a rabbit, a mouse, or a rat. An especially preferred patient is a human.

The phrase "pharmaceutically acceptable" refers to molecular entities and compositions that are "generally regarded as safe", e.g., that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

"Substantially greater affinity" means a binding affinity at least 1.5-fold greater for the target compound as compared to the standard compound and, more preferably, at least 10-fold greater and, most preferably, at least 100-fold greater. The selective antagonists are specific for denatured collagen type-IV (the target compound) and the binding affinities of the selective antagonists are compared to native collagen (the standard compound). Apparent binding affinity measurements can be made using enzyme linked immunosorbent assay (ELISA) or other techniques familiar to one of skill in the art, e.g., surface plasmon resonance technique (analyzed on a BIACORE 2000 system) (Liljeblad, et al. (2000) Glyco. J., Vol. 17: 323-329), and standard measurements and traditional binding assays (Heeley, R. P. (2002) Endocr. Res., Vol. 28: 217-229).

A "therapeutically effective amount" is an amount of selective denatured collagen antagonist sufficient to produce a measurable decrease in angiogenesis in the tissue being treated, i.e., an angiogenesis-inhibiting amount; or an amount of selective denatured collagen antagonist sufficient to produce a measurable decrease in tumor growth, metastasis, arthritis, inflammatory disease or condition associated denatured collage type-IV.

The term "treatment" is used herein to mean the administration of a denatured collagen type-IV selective antagonist to prevent angiogenesis, tumor growth, metastasis, bacterial invasion, arthritis, inflammation or any other disease or condition that is characterized or associated with denaturation of collagen type-IV or to inhibit the progression of pre-existing angiogenesis, tumor growth, metastasis, bacterial invasion, arthritis, inflammation or any other disease or condition that is characterize or associated with denaturation of collagen type-IV in a patient with such a disease or condition, and/or to ameliorate symptoms associated with such diseases or conditions.

The term "unit dose" when used in reference to a therapeutic composition of the present invention refers to a physically discrete unit suitable as a unitary dosage for the subject, each unit containing a predetermined quantity of active material calculated to produce the desired therapeutic effect either alone or in a composition comprising a suitable diluent; carrier, vehicle, or other excipient.

Denatured Collagen Type-IV Antagonists

The biologically active agents of the present invention comprise compounds that have a strong binding affinity for denatured collagen type-IV. A denatured collagen type-IV selective antagonist of the present invention has the amino acid core sequence L-K-Q-N-G-G-N-F-S-L.

One preferred denatured collagen type-IV selective antagonist for use in the present invention is CLK-peptide. CLK-peptide binds to denatured collagen type-IV with high specificity. The amino acid sequence of CLK peptide is NH2-C-L-K-Q-N-G-G-N-F-S-L-G-COOH. The CLK-peptide binds to regions within denatured collagen type-IV and inhibits cellular interactions with denatured collagen type-IV.

Adhesive cellular interactions with functional epitopes within the extracellular matrix have a role in regulating angiogenesis, tumor growth and metastasis in vivo. (Xu, J., et al. (2001) J. Cell Biol. Vol. 154:1069-1079; Hangai, et al. (2002) Am. J. Pathol. Vol. 161:1429-1437). CLK-peptide has been shown to potently block angiogenesis (Example 4 below) and tumor growth and metastasis (Example 5 below) in vivo.

It is well known in the art that modifications and changes can be made in the structure of a polypeptide without substantially altering the biological function of that peptide. For example, certain amino acids can be substituted for other amino acids in a given polypeptide without any appreciable loss of function. In making such changes, substitutions of like amino acid residues can be made on the basis of relative similarity of side-chain substituents, for example, their size, charge, hydrophobicity, hydrophilicity, and the like. These changes include substitutions or additions of amino acids at the termini of a peptide.

An amino acid sequence of the invention can include a sequence that is the same or substantially the same as a specifically recited SEQ ID NO. As used herein, the term "substantially" or "substantially the same" when used in reference to a nucleotide or amino acid sequence is intended to mean that the nucleotide or amino acid sequence shows a considerable degree, amount or extent of sequence identity when compared to a reference sequence. Such a considerable degree, amount or extent of sequence identity is further considered to be significant and meaningful and therefore exhibit characteristics which are definitively recognizable or known. Thus, a sequence which is substantially the same sequence as a sequence of the invention, including fragments thereof, refers to a sequence which exhibits characteristics that are definitively known or recognizable as encoding or as being the parent amino acid sequence. Minor modifications thereof are included so long as they are recognizable as a parent sequence. Similarly, an amino acid sequence which is substantially the same amino acid sequence as a sequence of the invention, or functional fragment thereof, refers to a sequence which exhibits characteristics that are definitively known or recognizable as representing the parent amino acid sequence and minor modifications thereof. When determining whether a nucleotide or amino acid sequence is substantially the same as a parent sequence, consideration is given to the number of changes relative to the parent sequence together with whether the function is maintained, for example, whether the function of binding to a cryptic collagen site is maintained for peptides of the invention.

Minor modification of these amino acids are intended to be included. Such minor modifications include, for example, those which do not change the encoded amino acid sequence due to the degeneracy of the genetic code as well as those which result in only a conservative substitution of the encoded amino acid sequence. Conservative substitutions of encoded amino acids include, for example, amino acids which belong within the following groups: (1) non-polar amino acids (Gly, Ala, Val, Leu, and Ile); (2) polar neutral amino acids (Cys, Met, Ser, Thr, Asn, and Gln); (3) polar acidic amino acids (Asp and Glu); (4) polar basic amino acids (Lys, Arg and His); and (5) aromatic amino acids (Phe, Trp, Tyr, and His). Other minor modifications are included within and at the ends of the peptides of the invention so long as the polypeptides retain some or all of their function as described herein.

As detailed in U.S. Pat. No. 4,554,101, incorporated herein by reference, the following hydrophilicity values have been assigned to amino acid residues: Arg (+3.0); Lys (+3.0); Asp (+3.0); Glu (+3.0); Ser (+0.3); Asn (+0.2); Gln (+0.2); Gly (0); Pro (0.5); Thr (−0.4); Ala (−0.5); His (−0.5); Cys (−1.0); Met (−1.3); Val (−1.5); Leu (−1.8); Ile (−1.8); Tyr (−2.3); Phe (−2.5); and Trp (−3.4). It is understood that an amino acid residue can be substituted for another having a similar hydrophilicity value (e.g., within a value of plus or minus 2.0) and still obtain a biologically equivalent polypeptide.

In a similar manner, substitutions can be made on the basis of similarity in hydropathic index. Each amino acid residue has been assigned a hydropathic index on the basis of its hydrophobicity and charge characteristics. Those hydropathic index values are: Ile (+4.5); Val (+4.2); Leu (+3.8); Phe (+2.8); Cys (+2.5); Met (+1.9); Ala (+1.8); Gly (−0.4); Thr (−0.7); Ser (−0.8); Trp (−0.9); Tyr (−1.3); Pro (−1.6); His (−3.2); Glu (−3.5); Gln (−3.5); Asp (−3.5); Asn (−3.5); Lys (−3.9); and Arg (−4.5). In making a substitution based on the hydropathic index, a value of within plus or minus 2.0 is preferred.

Another preferred selective denatured collagen type-IV antagonist for use in the present invention is SLK-peptide. SLK-peptide binds with high specificity to denatured collagen type-IV and inhibits cellular interactions with denatured collagen type-IV. The amino acid sequence of SLK-peptide is NH2-S-L-K-Q-N-G-G-N-F-S-L-C-COOH.

A further preferred selective denatured collagen type-IV antagonist for use in the present invention is KGGCLK peptide. KGGCLK peptide binds with high specificity to denatured collagen type-IV and inhibits cellular interactions with denatured collagen type-IV. The amino acid sequence of KGGCLK peptide is NH2-K-G-G-C-L-K-Q-N-G-G-N-F-S-L-G-G-K-COOH.

Sequential solid phase binding assays, for example, can be used to identify denatured collagen type-IV selective antagonists. Preferred methods for identifying denatured collagen type-IV antagonists are subtractive immunization (Xu, J. et al. (2000) Hybridoma, Vol. 19:375-385) and subtractive phage display (Example 1) (Amstutz P., et al. (2001) Curr. Opin. Biotechnol., vol. 12:400-405).

A preferred method of denaturation is thermal denaturation because thermal denaturation results in fewer small fragments that may have little immunogenicity in vivo. Collagen type-IV can be thermally denatured by, for example, heating collagen type-IV to 100° C. for fifteen minutes. Denaturation can also be accomplished by treating the collagen with a chaotropic agent. Suitable chaotropic agents include, for example, guanidinium salts. Collagen can also be denatured by ionizing radiation, non-ionizing radiation (ultraviolet), thermal injury, and mechanical stress or force. Collagen can be denatured by proteolysis. In particular, proteolyzed collagen can be prepared by treating the collagen with a metalloproteinase, such as MMP-1, MMP-2 or MMP-9, or by treating the collagen with a cellular extract containing collagen degrading activity. Proteolyzed collagen may also occur naturally at sites of neovascularization, tumor growth, metastasis, bacterial invasion, arthritis and inflammation in a tissue.

Denaturation of a collagen can be monitored, for example, by spectroscopic changes in optical properties such as absorbance, circular dichroism or fluorescence of the protein, by nuclear magnetic resonance, by Raman spectroscopy, or by any other suitable technique.

The resultant denatured collagen type-IV fragments can then be fixed to a solid matrix. Peptides known to bind collagen can be obtained from a peptide library. (Amstutz P., et al. (2001) Curr. Opin. Biotechnol., vol. 12:400-405). The collagen-binding peptides can be passed over the solid matrix. Peptides that bind denatured collagen type-IV adhere to the solid matrix. The adherent peptides can then be washed from the solid matrix and then passed over a second solid matrix to which native collagen type-IV is fixed. Peptides that do not bind to the second solid matrix are denatured collagen type-IV selective antagonists.

The selective peptide and polypeptide antagonists used in the present invention can be generated using several different techniques that are well known to those skilled in the art. For example, a two hybrid system (e.g., Fields, S. (1989) Nature 340:245-6) uses a collagen fragment as "bait" for selecting protein antagonists from a library that binds to the collagen peptide. This system and its operation are described in Green, D. M., et al., Proc. Natl. Acad. Sci. USA. 100:1010-1015 (2003) and in Gyuris, J. et al. (1993) Cell, Vol. 75: 791-803. The library of potential antagonists can be derived from a cDNA library, for example. In another embodiment, the potential antagonists can be variants of known collagen binding proteins such as integrins and fibronectin. (Hynes, R. O. (1992) Cell, Vol. 69:11-25; Steffensen, B., et al. (2002) Matrix Biol., Vol. 21:399-414; Ingham, K. C., et al. (2002) Arch. Biochem. Biophys., Vol. 407:217-223) Such proteins can be randomly mutagenized or subjected to gene shuffling, or other well known techniques for generating sequence diversity (Tani, P. H., et al. (2002) Biochm. J., Vol. 365:287-294; Stephanopoulos, G. (2002) Nat. Biotechnol., Vol. 20:666-668).

Peptide antagonists of the invention also can be generated using molecular evolution techniques as disclosed in Zhao, H., et al. (2002) Cur. Opin. Biotechnol., Vol. 13:104-110 and Guo, Z., et al. (2002) Biochemistry, Vol. 41:10603-10607. Libraries of proteins can be generated by mutagenesis, gene shuffling or other well known techniques for generating molecular diversity Protein pools representing numerous variants can be selected for their ability to bind to denatured collagen, for instance, by passing such protein pools over a solid matrix to which a denatured collagen has been attached. Elution with gradients of salt, for example, can provide purification of variants with affinity for the denatured collagen. A negative selection step also can be included whereby such pools are passed over a solid matrix to which native collagens have been attached. The filtrate will contain those variants within the pool that have a reduced affinity for the native form of the collagen.

The peptide and polypeptide antagonists of the present invention also can be generated by phage display. Phage display is a selection technique in which a peptide is expressed as a fusion with a coat protein of a bacteriophage. The result is that the fused protein is displayed on the surface of the virion and the DNA encoding the fusion protein resides within the virion. (Smith G. P. (1985) Filamentous fusion phage: Novel expression vectors that display cloned antigens on the virion surface. Science. 228:1315-1317; Smith G. P., et al. (1993) Libraries of peptides and proteins displayed on filamentous phage. Methods Enzymol. 217:228-257) Phage display allows for rapid identification of peptide ligands for a variety of target molecules using an in vitro process called panning. Panning is carried out, for example, by incubating a library of phage-displayed peptides with a microtiter plate coated with the target, washing away the unbound phage, and eluting the bound phage. The eluted phage is then amplified and taken through additional binding/amplification cycles to enrich the pool in favor of binding sequences. After 3-4 rounds of panning, individual clones are identified by DNA sequencing.

A randomized peptide or protein can be expressed on the surface of a phagemid (a term for the combination of phage and plasmid) particle as a fusion with a phage coat protein. Techniques of monovalent phage display are widely available (see, e.g., Lowman H. B. et al. (1991) Biochemistry 30:10832-8.) Phage expressing randomized peptide or protein libraries can be panned with a solid matrix to which a native collagen molecule has been attached. Remaining phage do not bind native collagens, or bind native collagens with substantially reduced affinity. The phage are then panned against a solid matrix to which a denatured collagen has been attached. Bound phage are isolated and separated from the solid matrix by either a change in solution conditions or, for a suitably designed construct, by proteolytic cleavage of a linker region connecting the phage coat protein with the randomized peptide or protein library. The isolated phage can be sequenced to determine the identity of the selected antagonist.

The well known ELISA assay can be used to identify collagen type-IV selective antagonists for use in practicing the present invention.

A peptide or polypeptide can be identified as an antagonist through the use of a solid phase ELISA to determine whether the peptide or polypeptide binds to denatured or native collagens. The ELISA assay is useful with a variety of collagen types; for example, the ELISA assay can be used with collagen types, I, II, III, IV and V, as well as for other extracellular matrix components. The level of binding affinity can be determined by surface plasmon resonance technique (analyzed on a BIACORE 2000 system) (Liljeblad, et al. (2000) Glyco. J., vol. 17:323-329) and standard measurements by traditional scatchard binding assays (Heeley, R. P. (2002) Endocr. Res., Vol. 28:217-229).

Solid phase ELISA also can be used to identify compounds which exhibit specificity for denatured, but not native, forms of collagen. The specificity assay is conducted by running parallel ELISAs where a potential antagonist is screened concurrently in separate assay chambers for the ability to bind denatured and native collagens.

Antagonists can also be identified by their ability to bind to a solid matrix containing a denatured collagen. Putative antagonists are collected after altering solution conditions, such as salt concentration, pH, temperature, etc. The putative antagonists are further identified by their ability to pass through, under appropriate solution conditions, a solid matrix to which a native collagen has been affixed.

The antagonists of the present invention can be used with collagen type-IV molecules from any invertebrate or vertebrate animal, including humans. Examples of collagen type-IV molecules are found in Engel, J. (1997) Science, Vol. 277:1785-1786 and Gordon, M. K., et al., (1990) Curr. Opin. Cell Biol., Vol. 2:833-838. Preferably, the collagen type-IV is a mammalian collagen type-IV. More preferably, the mammal is a pig, cow, goat, rabbit, mouse, rat, dog, cat, sheep, donkey, horse, or mule. In a particularly preferred embodiment, the collagen is human collagen type-IV.

The active agents for use in the invention comprise one or more denatured collagen type-IV antagonists. An antagonist of denatured collagen type-IV can be any peptide, polypeptide or peptido-mimetic that has substantially greater binding affinity to denatured collagen type-IV than to the native form of collagen type-IV.

The peptide antagonists of the present invention may be modified, for example, by phosphorylation, hydroxylation or methylation. Additional modifications that may enhance activity include peptide cyclization and peptide stabilization.

In another embodiment; the present invention includes analogs, fragments, or chemical derivatives of a polypeptide whose amino acid residue sequence is shown herein so long as the peptide is an antagonist of denatured collagen type-IV, but not of native collagen. Therefore, a peptide can be subject to various changes, substitutions, insertions, and deletions where such changes provide for certain advantages in its use. In this regard, a denatured collagen type-IV antagonist peptide of this invention includes the sequence of a recited peptide where one or more sequence changes are made and the peptide retains the ability to function as a denatured collagen type-IV selective antagonist in one or more of the assays as defined herein.

KGGCLK-peptide is one such modified peptide. KGGCLK-peptide is CLK-peptide with sequence KGG added to the N-terminus and GKA added to the C-terminus. The coupling of the amino acids may be accomplished by techniques familiar to those in the art and provided, for example, in Stewart and Young, 1984, Solid Phase Synthesis, Second Edition, Pierce Chemical Co., Rockford, Ill.

The antagonist can be conjugated with cytotoxins such as cisplatin, vinblastine and gemcitabine, for delivery to a tumor or other tissue undergoing angiogenesis, tumor growth, metastasis, arthritis or other disease or condition associated with cellular interactions with denatured collagen type-IV. Such conjugates can be made with a cytolysin or an exotoxin, for example ricin A, diphtheria toxin A, or Pseudomonas exotoxin and fragments thereof. The cytotoxic agent can also be radioactively labeled with an isotope so as to locally deliver a toxic dose of radioactivity to an angiogenic tissue, tumor growth, metastasis or other tissue undergoing cellular interaction with denatured collagen type-IV.

The antagonist can be conjugated with a cytostatic agent such as an anti-angiogenic compound, for delivery to a tumor or other tissue undergoing angiogenesis, tumor growth, metastasis, arthritis or other disease or condition associated with cellular interactions with denatured collagen type-IV. A preferred cytostatic agent is a matrix metalloproteinase (MMP) inhibitor. A preferred MMP inhibitor is Marimistat (British Biotech, Oxford, United Kingdom).

In Vivo Assays for Angiogenesis Inhibition

The selective peptide antagonists of the present invention can be assayed for their ability to modulate angiogenesis in a tissue. Any suitable assay known to one of skill in the art, such as the chick chorioallantoic membrane (CAM) assay, or the rabbit eye assay, or the chimeric mouse assay can be used to monitor such effects. Several non-limiting techniques are described herein.

One angiogenesis assay measures angiogenesis in the chick chorioallantoic membrane (CAM) and is referred to as the CAM assay. The CAM assay is well known among those of ordinary skill in the art and has been used to measure both angiogenesis and neovascularization of tumor tissues (Ausprunk et al., Am. J. Pathol., 79:597-618 (1975) and Ossonski et al., Cancer Res., 40:2300-2309 (1980)).

During the CAM assay, angiogenesis of whole tissue is occurring. The assay measures growth of chick embryo blood vessels into the CAM or into the tissue grown on the CAM. Accordingly, the CAM assay is a valid model for in vivo angiogenesis.

The CAM assay measures inhibition of angiogenesis based on both the amount and extent of new vessel growth. It is furthermore possible to monitor the growth of any tissue transplanted upon the CAM, such as a tumor tissue.

Finally, the CAM assay is particularly useful because there is an internal control for toxicity in the assay system. During the assay a viable, developing chick embryo is exposed to test reagent. The health of the embryo is an indication of toxicity.

In another assay, angiogenesis is measured in an in vivo rabbit eye model, referred to as the "rabbit eye assay". The rabbit eye assay is well known among those of ordinary skill in the art and has been used to measure both angiogenesis and neovascularization in the presence of angiogenic inhibitors such as thalidomide. (D'Amato et al. (1994) Proc. Natl. Acad. Sci. 91:4082-4085).

The rabbit eye assay is a well recognized assay model for in vivo angiogenesis because angiogenesis, exemplified by rabbit blood vessels growing from the rim of the cornea into the cornea, is easily visualized through the naturally transparent cornea of the eye. Additionally, both the extent and the amount of stimulation or inhibition of angiogenesis, or regression of angiogenesis, can easily be monitored over time.

The rabbit is exposed to any test reagent used, and therefore the health of the rabbit is an indication of toxicity of the test reagent.

Another assay measures angiogenesis in a chimeric mouse: human model and is referred to as the chimeric mouse assay. (Yan, et al. (1993) J Clin. Invest. 91:986-996). The chimeric mouse assay is a useful assay model for in vivo angiogenesis because the transplanted skin grafts closely resemble normal human skin histologically and neovascularization of whole tissue is occurring wherein actual human blood vessels are growing from the grafted human skin into the human tumor tissue on the surface of the grafted human skin. The origin of the neovascularization into the human graft can be demonstrated by immunohistochemical staining of the neovasculature with human-specific endothelial cell markers.

The chimeric mouse assay demonstrates regression of neovascularization based on both the amount and extent of regression of new vessel growth. Furthermore, effects on the growth of any tissue transplanted upon the grafted skin, such as a tumor tissue, may be monitored. Finally, the assay is useful because there is an internal control for toxicity in the assay system. The chimeric mouse is exposed to any test reagent used, and therefore the health of the mouse is an indication of toxicity.

Disease Treatment

The present invention relates generally to the discovery that binding of certain epitopes of denatured collagen type-IV, but not of native collagen type-IV, to selective antagonists inhibits angiogenesis, tumor growth, metastasis, arthritis, and other conditions or diseases associated with cellular interactions with denatured collagen type-IV in the tissues of mammals, including humans and other animals. Angiogenesis is required in a variety of disease processes. By inhibiting angiogenesis, one can intervene in the disease, ameliorate the symptoms, and in some cases cure the disease.

Where the growth of new blood vessels is required to support growth of abnormal tissue, inhibition of angiogenesis will reduce the blood supply to the tissue and thereby contribute to reduction in tissue mass based on blood supply requirements. Examples include growth of tumors, where neovascularization is a continual requirement in order that the tumor grow beyond a few millimeters in thickness, and for the establishment of solid tumor metastases. Where the growth of new blood vessels is the cause of, or contributes to, the pathology associated with a disease, inhibition of angiogenesis will reduce the deleterious effects of the disease. Examples include psoriasis, rheumatoid arthritis, diabetic retinopathy, inflammatory diseases, restenosis, macular degeneration and the like.

The methods of the present invention are effective in part because the therapy is highly selective for angiogenesis and other processes involving cellular interaction with denatured type-IV collagen, and not other biological processes. The discovery that binding of denatured collagens alone can effectively inhibit angiogenesis and other processes involving cellular interaction with denatured type-IV collagen allows for the development of therapeutic compositions with potentially high specificity, and therefore relatively low toxicity.

The present method for inhibiting angiogenesis in a tissue and, therefore, for practicing the methods for treatment of angiogenesis-related diseases, comprises administering to a patient in need of angiogenic treatment a composition comprising a therapeutically effective amount of a denatured collagen type-IV selective antagonist capable of binding selectively to denatured or proteolyzed collagen type-IV, compared to binding native collagen type-IV. Thus, the method comprises administering to a patient a therapeutically effective amount of a pharmaceutical composition comprising a denatured collagen type-IV selective antagonist of the invention.

The invention provides a method for inhibiting angiogenesis, tumor growth, metastasis, arthritis, inflammatory diseases and other diseases or conditions associated with cellular interactions with denatured collagen-type-IV in the tissue of an animal in need of such treatment, including mammals and humans, and, thereby, inhibiting events in the tissue which depend upon angiogenesis. Generally, the method comprises administering to an animal a composition comprising an effective angiogenesis-inhibiting amount of a denatured collagen type-IV selective antagonist.

The present invention also provides a method for inhibiting tumor neovascularization by inhibiting tumor angiogenesis. In certain embodiments, the tissue to be treated is a tumor tissue of a patient with a solid (malignant) tumor, a metastases, a skin cancer, a breast cancer, a hemangioma or angiofibroma and the like cancer; and the angiogenesis to be inhibited is tumor tissue angiogenesis where there is neovascularization of a tumor tissue. Typical solid tumor tissues treatable by the present methods include lung, pancreas, breast, colon, laryngeal, ovarian, Kaposi's sarcoma and similar tissues. The methods and combinations of the present invention may also be used to treat solid tumors of various types.

The methods and combinations of the present invention may also be used for the treatment of neoplastic disorders selected from the group consisting of acral lentiginous melanoma, actinic keratoses, adenocarcinoma, adenoid cycstic carcinoma, adenomas, adenosarcoma, adenosquamous carcinoma, astrocytic tumors, bartholin gland carcinoma, basal cell carcinoma, bronchial gland carcinomas, capillary, carcinoids, carcinoma, carcinosarcoma, cavernous, cholangiocarcinoma, chondrosarcoma, choriod plexus papilloma/carcinoma, clear cell carcinoma, cystadenoma, endodermal sinus tumor, endometrial hyperplasia, endometrial stromal sarcoma, endometrioid adenocarcinoma, ependymal, epitheloid, Ewing's sarcoma, fibrolamellar, focal nodular hyperplasia, gastrinoma, germ cell tumors, glioblastoma, glucagonoma, hemangiblastomas, hemangioendothelioma, hemangiomas, hepatic adenoma, hepatic adenomatosis, hepatocellular carcinoma, insulinoma, intaepithelial neoplasia, interepithelial squamous cell neoplasia, invasive squamous cell carcinoma, large cell carcinoma, leiomyosarcoma, lentigo maligna melanomas, malignant melanoma, malignant mesothelial tumors, medulloblastoma, medulloepithelioma, melanoma, meningeal, mesothelial, metastatic carcinoma, mucoepidermoid carcinoma, neuroblastoma, neuroepithelial adenocarcinoma nodular melanoma, oat cell carcinoma, oligodendroglial, osteosarcoma, pancreatic polypeptide, papillary serous adenocarcinoma, pineal cell, pituitary tumors, plasmacytoma, pseudosarcoma, pulmonary blastoma, renal cell carcinoma, retinoblastoma, rhabdomyosarcoma, sarcoma, serous carcinoma, small cell carcinoma, soft tissue carcinomas, somatostatin-secreting tumor, squamous carcinoma, squamous cell carcinoma, submesothelial, superficial spreading melanoma, undifferentiatied carcinoma, uveal melanoma, verrucous carcinoma, vipoma, well differentiated carcinoma, and Wilm's tumor Inhibition of tumor tissue angiogenesis is a significant development because of the important role neovascularization plays in tumor growth. In the absence of neovascularization, tumor tissue does not obtain the required nutrients, slows in growth, ceases additional growth, regresses and ultimately becomes necrotic resulting in killing or eliminating the tumor. An additional significant development is the direct inhibition of tumor growth and metastasis by blocking tumor cell adherence to denatured collagen type-IV and, thereby, preventing the tumor cell from becoming established in the tissue.

The invention also embodies a method of inhibiting tumor growth by preventing angiogenesis in the tumor.

In another aspect, the invention provides methods for inhibiting tumor growth and the formation of metastases through administration of biologically active compositions comprising antagonists of denatured collagen type-IV. These methods are particularly effective because (1) formation of metastases requires denaturation of collagen and vascularization of a primary tumor so that the metastatic cancer cells can exit the primary tumor and (2) establishment of a tumor in a secondary site requires denaturation of collagen and neovascularization to support growth of the metastases.

Additionally, the invention provides methods for inhibiting tumor growth and metastasis by directly inhibiting tumor cell interaction with denatured collagen type-IV. A tumor cell must adhere to a tissue in order to establish itself in the tissue and, subsequently, grow. The methods and compositions of the present invention directly inhibit tumor cell adherence to tissue by blocking tumor cell interaction with denatured collagen type-IV.

In further embodiments, the invention enables any of the foregoing methods to be carried out in combination with other therapies such as, for example, chemotherapy directed against solid tumors or radiation therapy. An angiogenesis inhibitor may be administered to a patient in need of such treatment before, during, or after chemotherapy. Preferably an angiogenesis inhibitor is administered to a patient after a regimen of chemotherapy. At such time, the tumor tissue responds to the toxic assault by inducing angiogenesis in order to recover by the provision of blood and nutrients to the tumor tissue. It is also preferred to administer an angiogenesis inhibitor to a patient as a prophylaxis against metastases after surgery on the patient for the removal of solid tumors.

Cancer Radiation Therapy

Treatment of cancers using radiation therapy is well-known in the art and extensively described in the literature.

Radiation is used as a therapeutic treatment for many types of cancers and is delivered in various ways, depending on the disease, its location, and its stage. The radiation therapy may be whole body irradiation, e.g., external, or may be directed locally to a specific site or tissue in or on the body, e.g., internal. Typically, radiation therapy is administered in pulses over a period of time from about 1 to about 2 weeks. The radiation therapy may, however, be administered over longer periods of time. Optionally, the radiation therapy may be administered as a single dose, a fractionated dose, or as multiple, sequential doses.

Examples of radiation therapies include conformal radiation therapy, coronary artery brachytherapy, fast neutron radiotherapy, intensity modulated radiotherapy (IMRT), interoperative radiotherapy, interstitial brachytherapy, interstitial breast brachytherapy, organ preservation therapy, and steriotactic radiosurgery. External beam radiation therapy for the treatment of cancer uses a radiation source that is external to the patient, typically either a radioisotope, such as 60Co, 137Cs, or a high energy x-ray source, such as a linear accelerator. The external source produces a collimated beam directed into the patient to the tumor site. External-source radiation therapy avoids some of the problems of internal-source radiation therapy, but it can irradiate non-tumorous or healthy tissue in the path of the radiation beam along with the tumorous tissue.

For administration of external beam radiation, the amount can be at least about 1 Gray (Gy) fractions at least once every other day to a treatment volume. In a particular embodiment, the radiation is administered in at least about 2 Gray (Gy) fractions at least once per day to a treatment volume. In another particular embodiment, the radiation is administered in at least about 2 Gray (Gy) fractions at least once per day to a treatment volume for five consecutive days per week. In another particular embodiment, radiation is administered in 10 Gy fractions every other day, three times per week to a treatment volume. In another particular embodiment, a total of at least about 20 Gy is administered to a patient in need thereof. In another particular embodiment, at least about 30 Gy is administered to a patient in need thereof. In another particular embodiment, at least about 40 Gy is administered to a patient in need thereof.

Typically, the patient receives external beam therapy four or five times a week. An entire course of treatment usually lasts from one to seven weeks depending on the type of cancer and the goal of treatment. For example, a patient can receive a dose of 2 Gy/day over 30 days.

The adverse effect of irradiating of healthy tissue can be reduced, while maintaining a given dose of radiation in the tumorous tissue, by projecting the external radiation beam into the patient at a variety of "gantry" angles with the beams converging on the tumor site. The particular volume elements of healthy tissue, along the path of the radiation beam, change, reducing the total dose to each such element of healthy tissue during the entire treatment.

The irradiation of healthy tissue also can be reduced by tightly collimating the radiation beam to the general cross section of the tumor taken perpendicular to the axis of the radiation beam. Numerous systems exist for producing such a circumferential collimation, some of which use multiple sliding shutters which, piecewise, can generate a radio-opaque mask of arbitrary outline.

The use of therapeutic radiopharmaceuticals is also encompassed by the invention. A radiopharmaceutical agent refers to a pharmaceutical agent which contains at least one radiation-emitting radioisotope. Examples of radiotherapeutic agents are provided in, but not limited to, radiation therapy and is known in the art (Hellman, Principles of Radiation Therapy, Cancer, in Principles and Practice of Oncology, 248-75 (Devita et al., ed., 4th edit., volume 1, 1993). Radiopharmaceutical agents are routinely used in nuclear medicine for the diagnosis and/or therapy of various diseases. The radiolabelled pharmaceutical agent, for example, a radiolabelled antibody, contains a radioisotope (RI) which serves' as the radiation source. As contemplated herein, the term "radioisotope" includes metallic and non-metallic radioisotopes. The radioisotope is chosen based on the medical application of the radiolabeled pharmaceutical agents. When the radioisotope is a metallic radioisotope, a chelator is typically employed to bind the metallic radioisotope to the rest of the molecule. When the radioisotope is a non-metallic radioisotope, the non-metallic radioisotope is typically linked directly, or via a linker, to the rest of the molecule.

Suitable metallic radioisotopes include, but are not limited to: Actinium-225, Antimony-124, Antimony-125, Arsenic-74, Barium-103, Barium-140, Beryllium-7, Bismuth-206, Bismuth-207, Bismuth212, Bismuth213, Cadmium-109, Cadmium-115m, Calcium-45, Cerium-139, Cerium-141, Cerium-144, Cesium-137, Chromium-51, Cobalt-55, Cobalt-56, Cobalt-57, Cobalt-58, Cobalt-60, Cobalt-64, Copper-60, Copper-62, Copper-64, Copper-67, Erbium-169, Europium-152, Gallium-64, Gallium-67, Gallium-68, Gadolinium153, Gadolinium-157 Gold-195, Gold-199, Hafnium-175, Hafnium-175-181, Holmium-166, Indium-110, Indium-111, Iridium-192, Iron 55, Iron-59, Krypton85, Lead-203, Lead-210, Lutetium-177, Manganese-54, Mercury-197, Mercury203, Molybdenum-99, Neodymium-147, Neptunium-237, Nickel-63, Niobium95, Osmium-185+191, Palladium-103, Palladium-109, Platinum-195m, Praseodymium-143, Promethium-147, Promethium-149, Protactinium-233, Radium-226, Rhenium-186, Rhenium-188, Rubidium-86, Ruthenium-97, Ruthenium-103, Ruthenium-105, Ruthenium-106, Samarium-153, Scandium-44, Scandium-46, Scandium-47, Selenium-75, Silver-10m, Silver-111, Sodium-22, Strontium-85, Strontium-89, Strontium-90, Sulfur-35, Tantalum-182, Technetium-99m, Tellurium-125, Tellurium-132, Thallium-204, Thorium-228, Thorium-232, Thallium-170, Tin-113, Tin-114, Tin-117m, Titanium-44, Tungsten-185, Vanadium-48, Vanadium-49, Ytterbium-169, Yttrium-86, Yttrium-88, Yttrium-90, Yttrium-91, Zinc-65, Zirconium-89, and Zirconium-95.

Nonmetallic radioisotopes include any of those useful in a therapeutic or diagnostic procedure in vivo or in vitro. Examples include but are not limited to: Iodine-131, Iodine-125, Iodine-123, Phosphorus-32, Astatine-211, Fluorine-18, Carbon-11, Oxygen-15, Bromine-76, and Nitrogen-13.

Examples of therapeutic radiopharmaceuticals include, for example, P32 chromic phosphate colloid, P32 sodium chromate, Sr89 chloride, Sm153 EDTMP lexidronam, sodium iodide 1131, Y90 ibritumomab tiuxetan, Iodine 131 tositumomab, and Y90 microspheres. The antagonists of the invention can be administered to the patient concurrently or sequentially with radiation treatment and/or with a therapeutic radiopharmaceutical compound.

Following administration of the antagonists of the invention and radiation, the patient's cancer and physiological condition can be monitored in various ways well known to the skilled practitioner. For instance, tumor mass may be observed physically, by biopsy or by standard x-ray imaging techniques.

Identifying the most appropriate isotope for radiotherapy requires weighing a variety of factors. These include tumor uptake and retention, blood clearance, rate of radiation delivery, half-life and specific activity of the radioisotope, and the feasibility of large-scale production of the radioisotope in an economical fashion. The key point for a therapeutic radiopharmaceutical is to deliver the requisite amount of radiation dose to the tumor cells and to achieve a cytotoxic or tumoricidal effect while not causing unmanageable side-effects.

It is preferred that the physical half-life of the therapeutic radioisotope be similar to the biological half-life of the radiopharmaceutical at the tumor site. For example, if the half-life of the radioisotope is too short, much of the decay will have occurred before the radiopharmaceutical has reached maximum target/background ratio. On the other hand, too long a half-life would cause unnecessary radiation dose to normal tissues. Ideally, the radioisotope should have a long enough half-life to attain a minimum dose rate and to irradiate all the cells during the most radiation sensitive phases of the cell cycle. In addition, the half-life of a radioisotope has to be long enough to allow adequate time for manufacturing, release, and transportation.

Other practical considerations in selecting a radioisotope for a given application in tumor therapy are availability and quality. The purity has to be sufficient and reproducible, as trace amounts of impurities can affect the radiolabeling and radiochemical purity of the radiopharmaceutical.

The type of radiation that is suitable for use in the methods of the present invention can vary. For example, radiation can be electromagnetic or particulate in nature. Electromagnetic radiation useful in the practice of this invention includes, but is not limited to, x-rays and gamma rays. Particulate radiation useful in the practice of this invention includes, but is not limited to, electron beams (beta particles), protons beams, neutron beams, alpha particles, and negative pi mesons. The radiation can be delivered using conventional radiological treatment apparatus and methods, and by intraoperative and stereotactic methods. Additional discussion regarding radiation treatments suitable for use in the practice of this invention can be found throughout Steven A. Leibel et al., Textbook of Radiation Oncology (1998) (publ. W. B. Saunders Company), and particularly in Chapters 13 and 14. Radiation can also be delivered by other methods such as targeted delivery, for example by radioactive "seeds," or by systemic delivery of targeted radioactive conjugates. J. Padawer et al., Combined Treatment with Radioestradiol lucanthone in Mouse C3HBA Mammary Adenocarcinoma and with Estradiol lucanthone in an Estrogen Bioassay, Int. J. Radiat. Oncol. Biol. Phys. 7:347-357 (1981). Other radiation delivery methods can be used in the practice of this invention.

For tumor therapy, both α and β-particle emitters have been investigated. Alpha particles are particularly good cytotoxic agents because they dissipate a large amount of energy within one or two cell diameters. The β-particle emitters have a relatively long penetration range (2-12 mm in the tissue) depending on the energy level. The long-range penetration is particularly important for solid tumors that have heterogeneous blood flow and/or receptor expression. The β-particle emitters yield a more homogeneous dose distribution even when they are heterogeneously distributed within the target tissue.

Radiotherapy and combination treatments resulting in enhanced radiosensitivity, are discussed at length in the art, e.g., in U. S. Publication Nos. 2005/0196340, 2004/0053935, 2005/0222183, and 2004/0018968, all incorporated herein by reference.

Sensitization to Radiation Treatment

One measure of an increase in the effectiveness of tumor radiation treatment, or sensitization to radiation treatment, is an increase in the therapeutic index of the radiation treatment. It is known to those of skill in the art that the therapeutic index of a treatment is a comparison of the amount that causes the therapeutic effect to the amount that causes toxic effects. Quantitatively, it is the ratio of the dose required to produce the desired therapeutic effect and the toxic dose. A commonly used measure of therapeutic index is the effective dose of a treatment for 50% of the population (ED50) divided by the lethal dose for 50% of the population (LD50).

Other measures known to those of skill in the art and described in the literature include analyses of tumor growth, including, but not limited to, a reduction in tumor growth rate, a decrease in tumor volume, and alteration in the expression of proteins, the levels of which are indicative of tumor growth. Furthermore, a reduced toxicity profile in conjunction with a promising tumor growth analysis would be an additional parameter for consideration in evaluating the effectiveness of tumor radiation treatment, or in the sensitization to radiation treatment. Methods of evaluating tumor growth, tumor cell adhesion, proliferation, and migration are known in the art and described herein in the Examples.

As discussed in, e.g., U. S. Publication No. 2005/0123945, incorporated herein in its entirety by reference, criteria for determining a tumor response to treatment with radiation therapy are widely accepted and enable comparisons of the efficacy alternative treatments (see Slapak and Kufe, Principles of Cancer Therapy, in Harrison's Principles of Internal Medicine, 13th edition, eds. Isselbacher et al., McGraw-Hill, Inc. 1994). A complete response (or complete remission) is described as the disappearance of all detectable malignant disease. A partial response is described as an approximately 50 percent decrease in the product of the greatest perpendicular diameters of one or more lesions. There can be no increase in size of any lesion or the appearance of new lesions. Progressive disease means at least an approximately 25 percent increase in the product of the greatest perpendicular diameter of one lesion or the appearance of new lesions. The response to treatment can be evaluated after completion of therapy.

As illustrated in Examples 20, 21 and 22 below, increased effectiveness of tumor radiation treatment and enhanced radiosensitivity is indicated by a substantial decrease in proliferation or tumor growth when the tumor cells are treated with an antagonist of the invention.

Combination Treatments

It is recognized in the art that a benefit of using radiation therapy or chemotherapy in conjunction with other therapies, e.g., the antagonists of the present invention, can be useful for allowing administration of lower doses of radiation or chemotherapeutic agents, thereby potentially resulting in a reduction in toxic side effects. It is also known to those of skill in the art that therapeutically-effective dosages of radiation or chemotherapeutic agents can vary when these drugs are used in treatment combinations. Methods for experimentally determining therapeutically-effective dosages of chemotherapeutic drugs and other agents for use in combination treatment regimens are described in the literature. For example, the use of metronomic dosing, i.e., providing more frequent, lower doses in order to minimize toxic side effects, has been described extensively in the literature.

A combination treatment regimen encompasses treatment regimens in which administration of radiation or a chemotherapeutic agent is initiated prior to, during, or after treatment with the second agent, e.g., peptide of the invention, and continues until any time during treatment with the other agent or after termination of treatment with the other agent. It also includes treatments in which the agents being used in combination are administered simultaneously or at different times and/or at decreasing or increasing intervals during the treatment period. Combination treatment includes periodic treatments that start and stop at various times to assist with the clinical management of the patient. For example, an agent in the combination can be administered weekly at the onset of treatment, decreasing to biweekly, and decreasing further as appropriate.

Accordingly, the methods of inhibiting tumor growth, metastasis, and neovascularization disclosed in this application can be applied to inhibit tumor tissue growth, to inhibit tumor metastases formation, and to cause regression of established tumors.

There are a variety of diseases besides cancer in which angiogenesis is believed to be important. These are referred to as angiogenic diseases, including but not limited to, inflammatory disorders such as immune and non-immune inflammation, chronic articular rheumatism and psoriasis; disorders associated with inappropriate or inopportune invasion of vessels such as diabetic retinopathy, neovascular glaucoma, restenosis, capillary proliferation in atherosclerotic plaques and osteoporosis; and cancer associated disorders, such as solid tumors, solid tumor metastases, angiofibromas, retrolental fibroplasia, hemangiomas, Kaposi's sarcoma and the like cancers which require neovascularization to support tumor growth. Other suitable tumors include melanoma, carcinoma, sarcoma, fibrosarcoma, glioma and astrocytoma.

Thus, methods which inhibit angiogenesis in a diseased tissue treat and ameliorate symptoms of the disease and, depending upon the disease, can contribute to a cure.

In one embodiment, the present invention contemplates a method for inhibition of angiogenesis in a mammalian, e.g. human, tissue by administration of a denatured collagen type-IV selective antagonist.

As described herein, any of a variety of tissues, or organs comprised of organized tissues, can support angiogenesis in disease conditions including skin, muscle, gut, connective tissue, joints, bones and the like tissue, in which blood vessels can invade upon angiogenic stimuli. Tissue, as used herein, encompasses all bodily fluids, secretions and the like, such as, for example, serum, blood, cerebrospinal fluid, plasma, urine, synovial fluid, vitreous humor.

Thus, in one related embodiment, the tissue to be treated is an inflamed tissue and the angiogenesis to be inhibited is inflamed tissue angiogenesis where there is neovascularization of inflamed tissue. In this class, the method contemplates inhibition of angiogenesis in arthritic tissues (e.g., such as in a patient with chronic articular rheumatism), in immune or non-immune inflamed tissues, (e.g., in psoriatic tissue).

In another embodiment, the tissue to be treated is a retinal tissue of a patient with diabetic retinopathy, macular degeneration or neovascular-glaucoma and the angiogenesis to be inhibited is retinal tissue angiogenesis where there is neovascularization of retinal tissue.

Restenosis is a process of smooth muscle cell (SMC) migration and proliferation at the site of previous stenosis in a blood vessel. The migration and proliferation of SMCs associated with blood vessels during restenosis is related to the process of angiogenesis which is inhibited by the present methods and compositions. The invention also contemplates inhibition of restenosis by inhibiting angiogenic related processes according to the present methods and compositions in a patient following a procedure to correct vascular stenosis. Accordingly, the methods and compositions disclosed herein can be used at sites of percutaneous transluminal coronary angioplasty, coronary artery bypass, peripheral artery bypass, mesenteric artery bypass, and carotid endarterectomy or angioplasty.

The dose ranges for the administration of the denatured collagen type-IV selective antagonist depend upon the form of the antagonist and its potency, and are amounts large enough to produce the desired effect in which angiogenesis and the disease symptoms mediated by angiogenesis are ameliorated. The dosage should not be so large as to cause adverse side effects such as hyperviscosity syndromes, pulmonary edema, congestive heart failure, and the like. Generally, the dose will vary with the age, condition, sex and extent of the disease in the patient and can be determined by one of skill in the art. The dose also can be adjusted by the physician in the event of any complication.

Potency of a denatured collagen type-IV selective antagonist can be measured by a variety of means including, for example, inhibition of angiogenesis in the CAM assay, in the in vivo rabbit eye assay, or in the in vivo chimeric mouse: human assay as discussed herein.

A therapeutically effective amount of a denatured collagen type-IV antagonist of this invention is typically an amount of peptide such that when administered in a pharmaceutically acceptable composition is sufficient to achieve a plasma concentration of from about 0.1 microgram (µg) per milliliter (ml) to about 200 µg/ml, preferably from about 1 µg/ml to about 150 µg/ml. Based on a polypeptide having a mass of about 500 grams per mole, the preferred plasma concentration in molarity is from about 2 micromolar (µM) to about 5 millimolar (mM) and preferably about 100 µM to 1 mM polypeptide antagonist. Stated differently, the dose per body weight can vary from about 0. 1 mg/kg to about 300 mg/kg, and preferably from about 0.2 mg/kg to about 200 mg/kg, in one or more dose administrations daily, for one or several days.

Denatured collagen type-IV selective antagonists can be administered, for example, parenterally, by injection, or by gradual infusion over time. A preferred mode of administration for preventing angiogenesis is by intravenous administration of therapeutic compositions containing one or more of the biologically active agents of the present invention. Thus, antagonists and derivatives thereof can be administered intravenously, intraperitoneally, intramuscularly, subcutaneously, intracavity, transdermally, topically, intraocularly, orally, intranasally and can be delivered by peristaltic means. The therapeutic compositions of this invention may be administered intravenously, as by injection of a unit dose, for example.

In a preferred embodiment, the denatured collagen type-IV selective antagonist is administered in a single intravenous dose.

The compositions are administered in a manner compatible with the dosage formulation, and in a therapeutically effective amount. The quantity to be administered and timing depends on the patient to be treated, capacity of the patient's system to utilize the active ingredient, and degree of therapeutic effect desired. Precise amounts of active ingredient required to be administered depend on the judgment of the physician and are peculiar to each individual. However, suitable dose ranges for systemic application are disclosed herein and depend on the route of administration. Suitable regimes for administration also are variable, but are typified by an initial administration followed by repeated doses at one or more hour intervals by a subsequent injection or other administration. Alternatively, continuous intravenous infusion sufficient to maintain concentrations in the blood in the ranges specified for in vivo therapies are contemplated.

Inhibition of angiogenesis and tumor regression may occur as early as 7 days after the initial administration of the antagonist. Preferably, administration of antagonist is repeated resulting in tissue exposure to the antagonist for between 7 days and 6 weeks, more preferably between about 14 and 28 days.

For inhibition of restenosis, the denatured collagen type-IV selective antagonist is typically administered after the stenosis-relieving procedure for from about 2 to about 28 days, and more typically for about the first 14 days following the procedure.

Therapeutic Compositions

The present invention contemplates therapeutic compositions useful for practicing the therapeutic methods described herein. Therapeutic compositions of the present invention contain a pharmaceutically acceptable carrier together with a denatured collagen type-IV selective antagonist as described herein, dissolved or dispersed therein as an active ingredient. In a preferred embodiment, the therapeutic denatured collagen type-IV selective antagonist composition is not immunogenic when administered to a mammal or human patient for therapeutic purposes. One especially preferred denatured collagen type-IV selective antagonist is CLK peptide. Another preferred denatured collagen type-IV selective antagonist is SLK peptide. Another preferred denatured collagen type-IV selective antagonist is KGGCLK peptide.

The preparation of a pharmacological composition that contains active ingredients dissolved or dispersed therein is well understood in the art and need not be limited based on formulation. Typically such compositions are prepared as injectables either as liquid solutions or suspensions, however, solid forms suitable for solution, or suspensions, in liquid prior to use also can be prepared. The preparation also can be emulsified.

The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient.

The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups also can be derived from inorganic bases such as, for example, sodium, potassium, 3 ammonium, calcium or ferric hydroxides, and such organic bases as isopropylamine, trimethylamine, 2-ethylamino ethanol, histidine, procaine and the like. Particularly preferred are the salts of TFA and HCl.

Pharmaceutically acceptable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes.

Liquid compositions also can contain liquid phases in addition to and to the exclusion of water. Exemplary of such additional liquid phases are glycerin, vegetable oils such as cottonseed oil, and water-oil emulsions.

A therapeutic composition contains an angiogenesis-inhibiting, tumor growth-inhibiting, or metastasis-inhibiting amount of a denatured collagen type-IV selective antagonist of the present invention, formulated to contain 0.01 to 90 weight percent of antagonist per weight of total therapeutic composition. A preferred therapeutic composition formulation contains 0.05 to 50 weight percent of antagonist per weight of total therapeutic composition. A most preferred therapeutic composition formulation contains 0.1 to 20 weight percent of antagonist per weight of total therapeutic composition. A weight percent is a ratio by weight of inhibitor to total composition. Thus, for example, 0.1 weight percent is 0.1 grams of inhibitor per 100 grams of total composition.

Detection Methods

Denatured collagen type-IV antagonists of the invention also are suitable for detection of angiogenesis, tumor growth, arthritis or other diseases or conditions associated with cellular interaction with denatured collagen type-IV in tissues. Such methods of detection may be used ex vivo and in vivo. An ex vivo method, for example, is the detection of angiogenesis, tumor growth or metastasis in a biopsy specimen.

Binding of detectably labeled denatured collagen selective antagonists to target tissue can be detected either directly or indirectly. Direct detection can be preformed on said antagonists comprising a detectable label such as a fluorochrome, a radioactive tag, paramagnetic heavy metal or diagnostic dye.

Indirect detection is performed using a detectable secondary reagent that interacts with the denatured collagen type-IV selective antagonist. A detectably labeled antibody that recognizes said antagonist can be used, for example, to visualize the location of the antagonist. Other methods of indirect detection are also known to those of ordinary skill in the art.

In vivo imaging methods permit the detection of a labeled antagonist that specifically binds to denatured collagen type-IV in the subject's body. The labeled antagonist is administered to a patient e.g., intravenously or intramuscularly. In vivo detection methods include magnetic resonance spectroscopy, positron-emission tomography (PET) and single photon emission tomography (SPECT). For purposes of in vivo imaging, the type of detection instrument available is a major factor in selecting a given label. For instance, radioactive isotopes and paramagnetic isotopes are particularly suitable for in vivo imaging. The type of instrument used will guide the selection of the radionuclide. For instance, the radionuclide chosen must have a type of decay which is detectable for a given type of instrument. However, any conventional method for visualizing diagnostic imaging can be utilized in accordance with this invention. In one embodiment, a radionuclide may be bound to an antibody either directly or indirectly by using an intermediary functional group. Intermediary functional groups which are often used to bind radioisotopes which exist as metallic ions to antibody are diethylenetriaminepentaacetic acid (DTPA) and ethylene diaminetetracetic acid (EDTA). Examples of metallic ions suitable as radioactive isotopes are 99 mTc, 123 I, 131 I, 111In, 131I, 97Ru, 67Cu, 67Ga, 125I, 68Ga, 72As, 89Zr, and 201Tl. Examples of paramagnetic isotopes, particularly useful in Magnetic Resonance Imaging ("MRI"), include 157Gd, 55Mn, 162Dy, 52Cr, and 56Fe.

EXAMPLES

The following Examples illustrate the invention, but are not limiting.

Example 1

Generation of Peptides that Specifically Bind to Denatured Collagen Type-IV Epitopes Subtractive phage display was used to generate peptides that specifically bind to denatured collagen type-IV. Peptide were expressed as a fusion with a coat protein of a bacteriophage on the surface of a virion. Panning was carried out by incubating a library of phage-displayed peptides with a microtiter plate coated with the target (native collagen type-IV in wells 1-4, denatured collagen type-IV in well 5), washing away the unbound phage, and eluting the specifically-bound phage. The eluted phage was taken through repeated panning to enrich the pool in favor of binding sequences.

On day one, collagen type-IV at a concentration of 25 µg/ml was dissolved in 0.1M NaHCO3 (pH8.6) and then the solution was boiled for 15 minutes, thereby yielding thermally denatured collagen. Next, the solution was cooled to room temperature.

100 microliters of native collagen type-IV (unboiled) was added to four wells (Nunc-Immuno™ Maxisorp™ available from Nalge Nunc International, Rochester, N.Y.) and 100 microliters of denatured collagen type-IV (boiled) was added to a fifth well. The plate was swirled repeatedly until its surface was wet. The plate, with its top sealed, was incubated overnight at a temperature of 4° C. with a gentle agitation.

On day two, 10 ml of LB/tet medium was inoculated with a single colony of ER2738 *E. coli* strain. LB/tet medium was prepared as follows: A liter of LB medium was prepared from 10 g/l of Bacto-tryptone and 5 g/l NaCl. The mixture was autoclaved for 15 minutes at 121° C. and then stored at room temperature. Tetracycline stock was prepared using 20 mg/ml of tetracycline in ethanol, which was stored at minus 20° C. in the dark, and then vortexed prior to use. LB/tet plates were prepared from LB medium and 15 g/l agar, which was autoclaved for 15 minutes at 121° C. and cooled to less than 70° C. One ml of tetracycline stock was then added and the mixture was poured onto the plates. The plates were stored at 4° C. in the dark.

Coating solution was poured off the first well and the well was washed twice with TBST (TBS+0.1% (v/v) Tween-20). TBS was prepared from 50 mM Tris-HCl (pH 7.5) and 150 mM NaCl, which was autoclaved for 15 minutes at 121° C. and stored at room temperature.

Next, $2 \times 10^{11}$ phage (10 microliter of the original library, obtained from New England Bio Labs, Inc.) was diluted with 100 microliters of TBST and pipetted onto the first well. The first well was then rocked gently for 60 minutes at 4° C.

The coating solution of the second well was poured off and the well was washed twice with TBST. Supernatant from the first well was then pipetted onto the second well. The second well was rocked gently for 60 minutes at 4° C.

The coating solution of the third well was poured off and the well was washed twice with TBST. Supernatant from the second well was then pipetted onto the third well. The third well was rocked gently for 60 minutes at 4° C.

The coating solution of the fourth well was poured off and the well was washed twice with TBST. Supernatant from the third well was then pipetted onto the fourth well. The fourth well was rocked gently for 60 minutes at 4° C.

The coating solution of the fifth well was poured off and the well was filled with blocking buffer (0.1M NaHCO$_3$ (pH 8.6), 5 mg/ml BSA, 0.02% NaN$_3$, filter sterilized and stored at 4° C.). Next, the fifth well was incubated for 60 minutes at 4° C. The blocking buffer solution was then discarded and the fifth well was washed six times with TBST. Supernatant from the fourth well was then pipetted onto the fifth well and the fifth well was incubated for 60 minutes at room temperature. Next, the solution was poured off the fifth well and the fifth well was washed ten times with TBST.

The phage bound to the fifth plate was eluted with 0.2M glycine-HCl (pH 2.2). Following elution, the phage was amplified and titrated. The phage was then used for the next round of panning. The process of day two was repeated three times, each time using the phage produced at the end of the previous run.

The final step was isolation and identification of the peptides by sequence, which yielded CLK and SLK peptides.

Example 2

Peptide Antagonists of Denatured Collagen Type-IV Blocked Tumor Cell Adhesion to Denatured Collagen Type-IV In vitro cell adhesion assays were conducted to determine whether the CLK and SLK peptides bind to functional epitopes within denatured collagen type-IV that regulate cellular adhesion. Non-tissue culture treated 48-well plates were coated with denatured collagen type-IV. Human melanoma cells M21 (Scripps Research Institute, La Jolla, Calif.) were allowed to attach to the coated wells in the presence or absence of the synthetic peptides CLK, SLK, and SDR, each peptide was at a concentration of 250 µg/ml. SDR peptide is a commercially available peptide that was used as a control (QED Bioscience, Inc., San Diego, Calif.).

Human denatured collagen type-IV (25 µg/ml) was immobilized on 48-well nontissue culture treated plates. Wells were washed and incubated with 1% BSA (bovine serum albumin) in PBS (phosphate-buffered saline) for one hour at 37° C. Subconfluent HUVECs (human umbilical vein endothelial cells) were harvested, washed, and resuspended in adhesion buffer containing RPMI-1640 medium, 1 mM MgCl$_2$, 0.2 mM MnCl$_2$, and 0.5% BSA. HUVECs ($10^5$) were resuspended in 200 µl of the adhesion buffer in the presence or absence of each of the synthetic peptides and were added to each well and allowed to attach for 30 minutes at 37° C. The unattached cells were removed and the attached cells were stained for 10 minutes with crystal violet as described by Petitclerc, et al. (1999) Integrin αvβ3 promotes M21 melanoma growth in human skin by regulating tumor cell survival. Cancer Res. 59:2724-2730. The wells were washed three times with PBS and cell-associated crystal violet was eluted by addition of 100 µl of 10% acetic acid. Cell adhesion was quantified by measuring the optical density of eluted crystal violet at a wavelength of 600 nm.

CLK-peptide blockade of melanoma cell adhesion exceeded 95% (FIG. 1). SLK-peptide blocked melanoma cell adhesion by about 50%.

Example 3

CLK-Peptide Blocked B16 Melanoma Cell Adhesion to Denatured Collagen Type-IV

Figure 2:
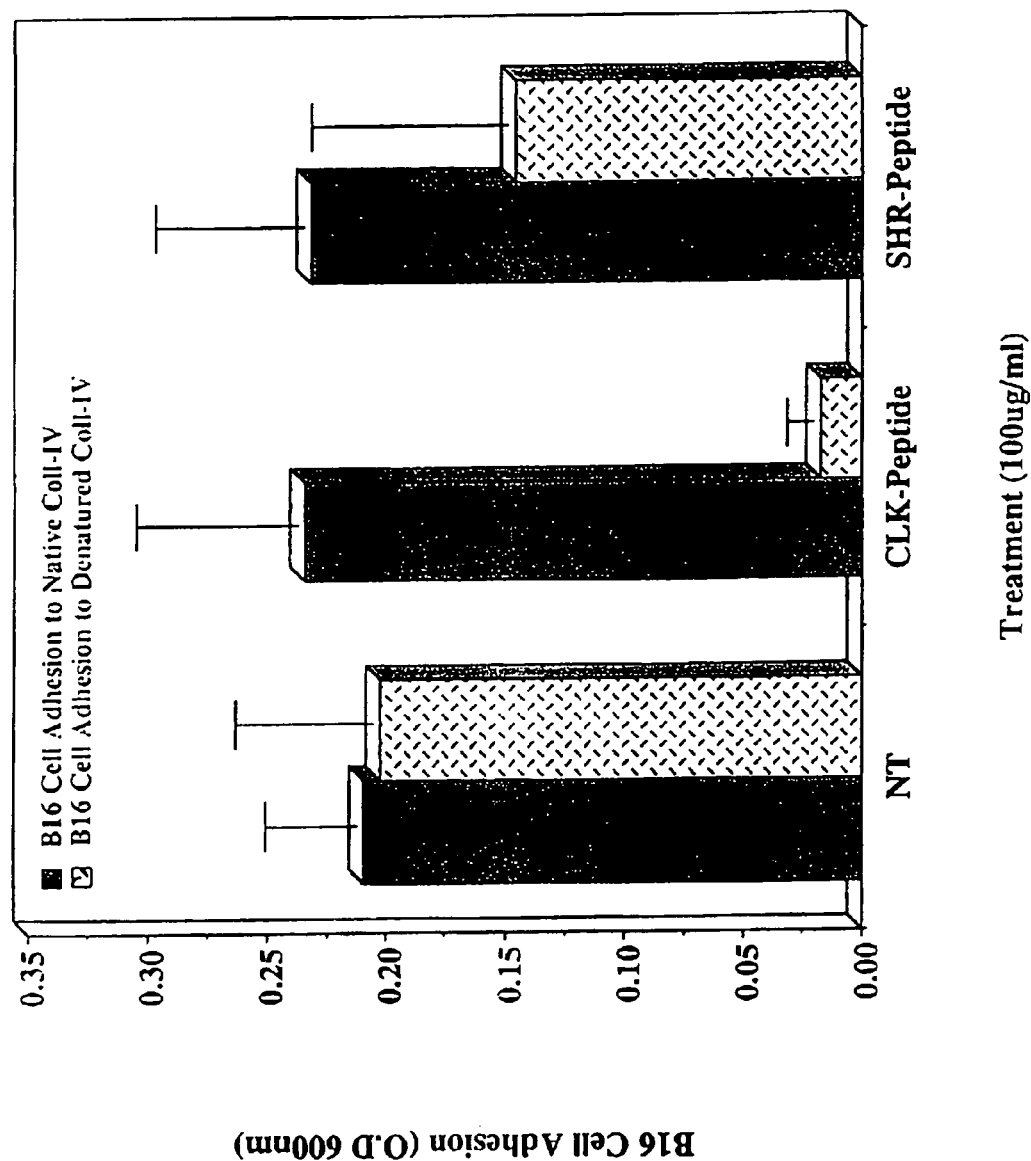
FIG. 2 is a chart which illustrates B16 murine melanoma cell adhesion to untreated denatured collagen type-IV (NT), CLK-peptide treated denatured collagen type-IV, and SHR-peptide treated denatured collagen type-IV.

Non-tissue culture treated 48-well plates were coated with either native (triple helical) or denatured collagen type-IV. Metastatic B16 murine melanoma cells were allowed to attach to the coated wells in the presence or absence of either CLK or SHR (control) peptide. CLK-peptide blockade of B16 cell adhesion to denatured type-IV collagen exceeded 95% (FIG. 2). CLK-peptide had little effect on B16 melanoma cell adhesion to native collagen type-IV.

Example 4

CLK-Peptide Blocked bFGF-Induced Angiogenesis in the Chick CAM Model

Figure 3:
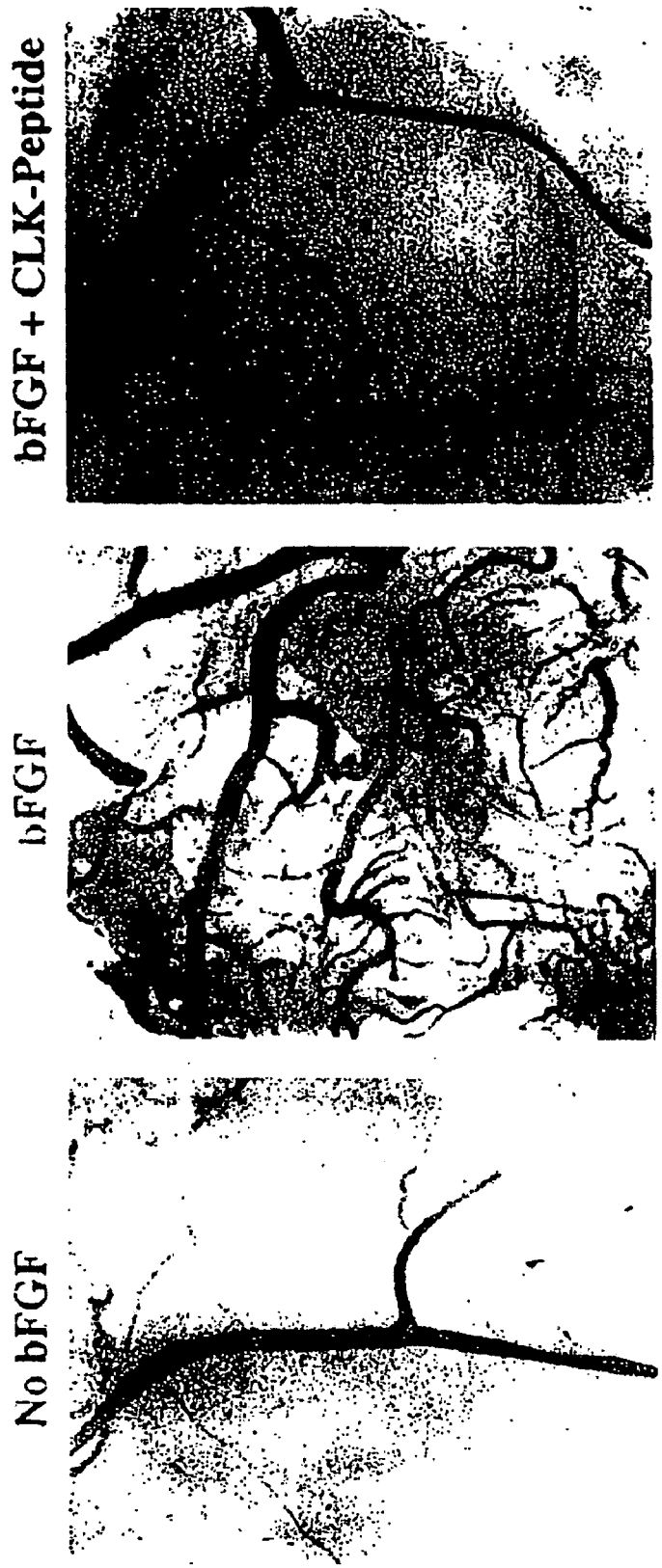
FIGS. 3(a), (b), and (c) depict a chick chorioallantoic membrane (CAM) without bFGF-induced angiogenesis, a CAM following bFGF-induced angiogenesis, and a CAM treated with CLK-peptide after bFGF-induced angiogenesis.
Figure 4:
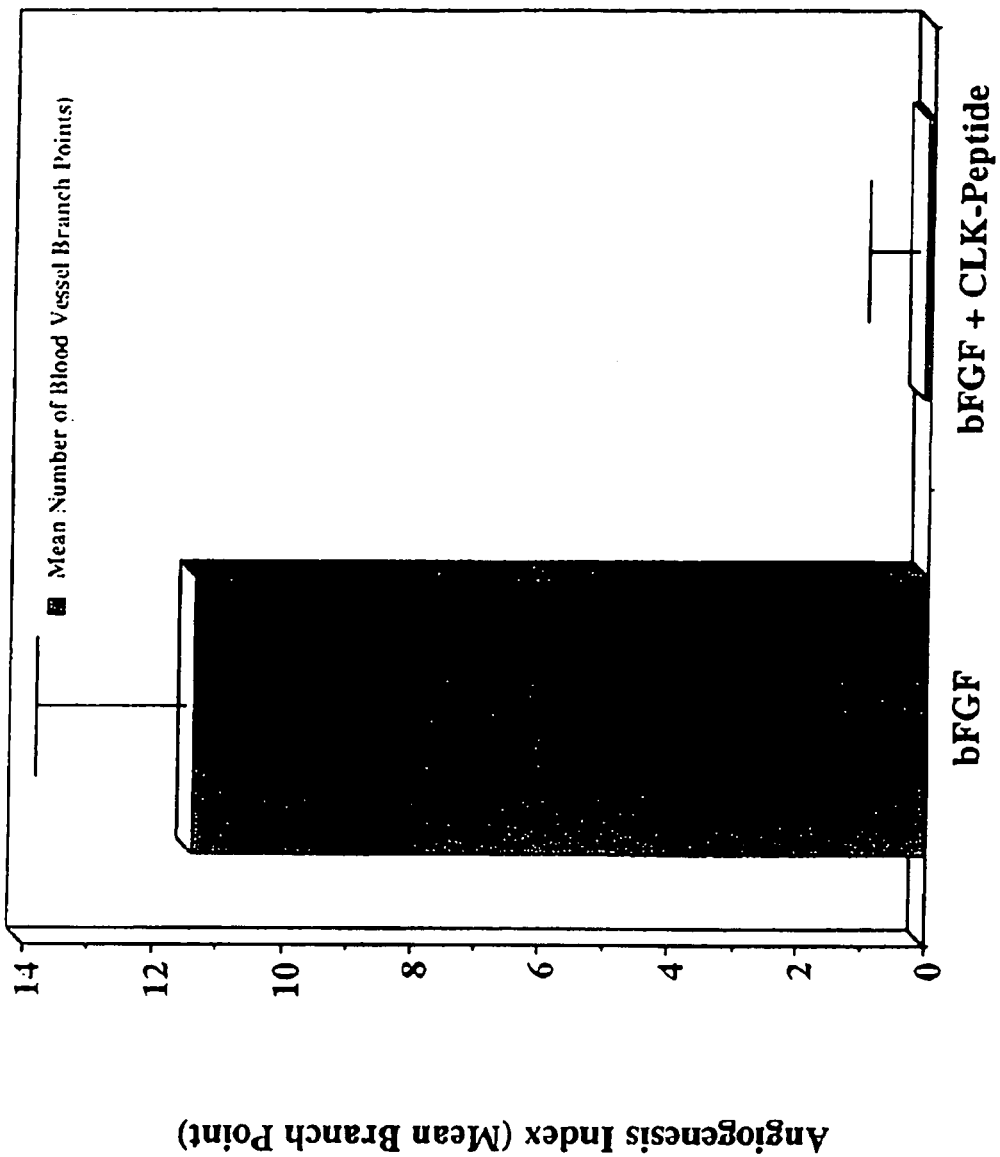
FIG. 4 is a chart which illustrates quantification of CAM angiogenic blood vessels following bFGF-induced angiogenesis without subsequent CLK-peptide treatment and CAM angiogenic blood vessels following bFGF-induced angiogenesis with subsequent CLK-peptide treatment.

Angiogenesis was induced within the chorioallantoic membrane (CAM) of 10-day old chick embryos with bFGF. Twenty-four hours later, 8-10 of the embryos were treated with a single intravenous injection of CLK-peptide (100 ug/embryo). At the end of a 3-day incubation period, the CAM tissues were removed for analysis. The injection of CLK-peptide resulted in a dramatic reduction in the number of branching vessels within the confined area of the filter disc. (FIG. 3(a),(b),(c)) The single injection of CLK-peptide inhibited bFGF by greater than 95%. (FIG. 4) No adverse effects were noted following injection of the peptide. Eight to ten chick embryos were tested in each of the two groups, and the experiment was repeated three times for a total of 24-30 chick embryos tested.

Example 5

CLK-Peptide Inhibited B16 Melanoma Metastasis in vivo

Figure 5:
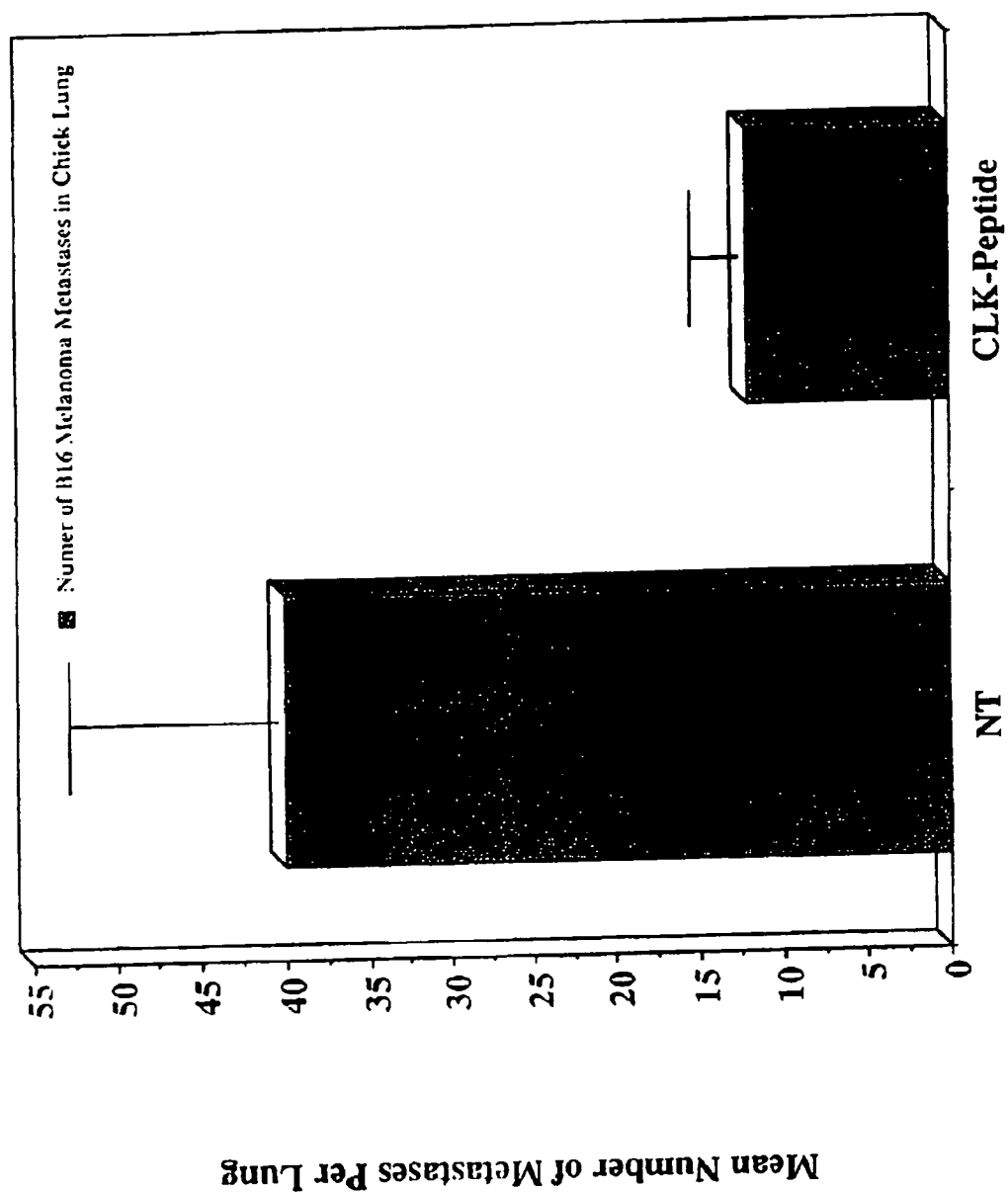
FIG. 5 is a chart, which illustrates quantification of B16 melanoma metastases on chick embryo lungs untreated with CLK-peptide (NT) and chick embryo lungs treated with CLK-peptide.

Twelve-day old chick embryos (obtained from SPAFAS, North Franklin, Conn.) were injected intravenously with metastatic B16 melanoma cells (Chambers, et al. (1992) J. Natl. Cancer Inst., Vol. 84:797-803) in the presence or absence of CLK-peptide (100 ug/embryo). For each experiment, eight to ten chicks were tested under each set of conditions, and the experiment was repeated three times. The embryos were incubated for 7 days and then sacrificed. The chick lungs were analyzed for metastasis. B16 melanoma metastases appeared as discrete black lesions. The metastases were quantified by counting the B16 tumor lesions on the surface of the chick lungs for the CLK and no-CLK groups. B16 melanoma metastasis was inhibited by about 70% in the CLK group as compared to the no-CLK group. (FIG. 5)

Example 6

Treatment of a Patient with Metastatic Breast Cancer

A 60 kilogram patient with breast cancer metastatic to the liver has blood drawn for liver function tests. The patient undergoes an abdominal CT scan in order to note the size and number of the liver metastases. The patient's overall medical condition is assessed by a health professional using physical examination; blood tests such as a complete blood count, BUN, and creatinine; and EKG.

A CLK-peptide dose of 9000 milligrams is calculated by multiplying the patient's weight (60 kilograms) by the dose per body weight (150 milligrams per kilogram). The CLK-peptide dose is mixed in aqueous solution and administered intravenously through a peripheral vein catheter over a 2 hour period. Following infusion of CLK-peptide, the patient is monitored for 2 hours by a health professional for the appearance of adverse effects. In the absence of such effects, the patient is discharged home.

Two weeks following CLK-peptide infusion, the patient has repeat liver function tests and CT scan. Lowering of the liver function test values may be indicative of tumor metastases regression. CT scan visualization of decreased size and/or number of metastases is indicative of successful treatment of the metastases.

Example 7

CLK-Peptide Inhibits Endothelial Cord Formation In Vitro

Figure 6:
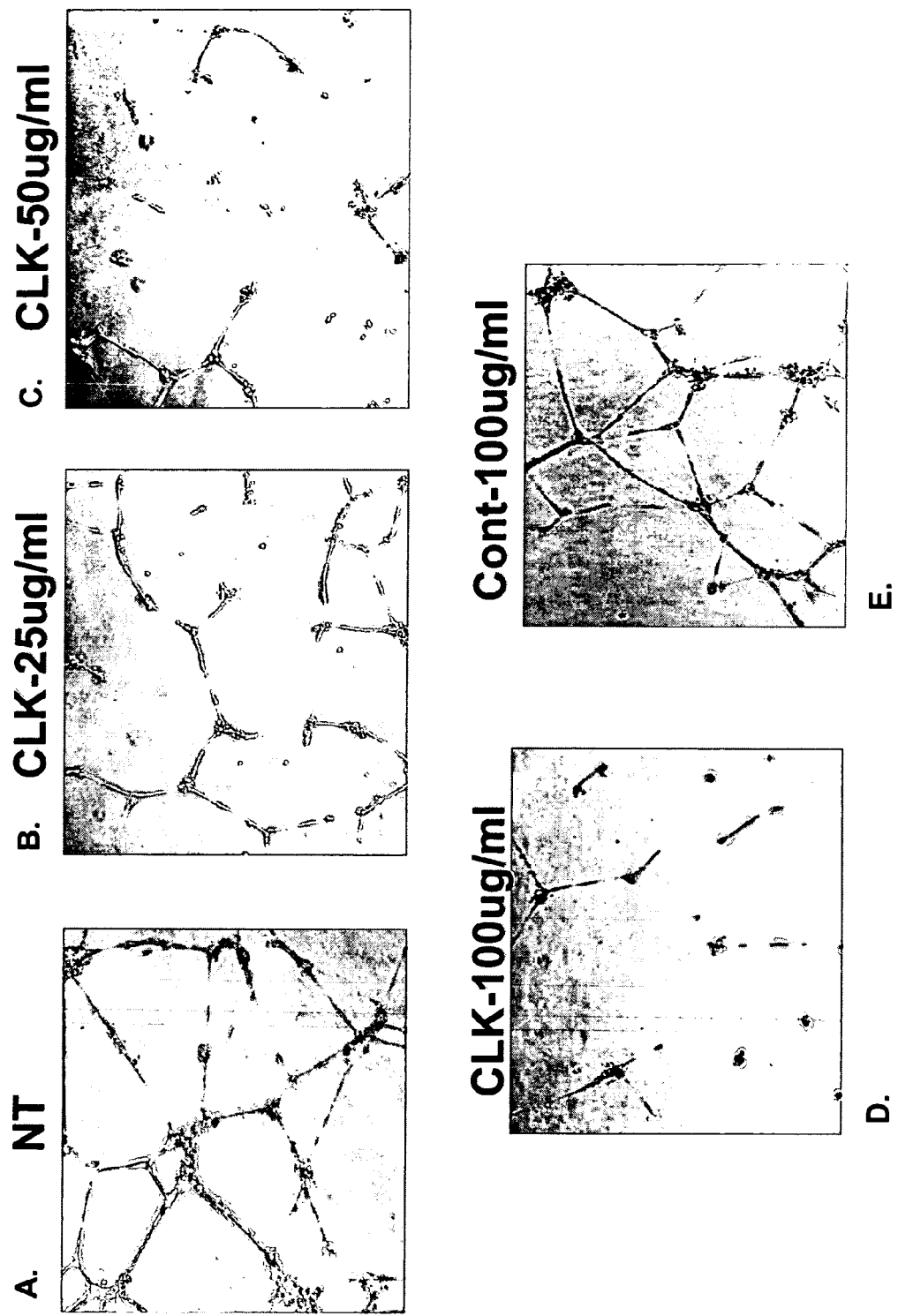
FIG. 6 Effects of CLK Peptide on HUVEC Cord Formation in MATRIGEL®. MATRIGEL was added to 96-well plates and allowed to form three-dimensional gels. Human endothelial cells (HUVECs) were resuspended in the presence or absence of CLK-Peptide or the inactive control peptide CTW, derived from our subtractive phage display protocol (having the amino acid sequence CTWPRHHTTDALL) (0-100 µg/ml), and allowed to form cords in MATRIGEL for 24 hours. Representative photos were taken at a magnification of 100×. A. Untreated control. B. CLK 25 µg/ml C. CLK 50 µg/ml D. CLK 100 µg/ml E. Control Peptide 100 µg/ml.

The role that the CLK cryptic collagen epitope plays in regulating endothelial cell morphogenesis and cord formation, processes important in angiogenesis, were investigated. MATRIGEL was diluted in M199 medium and 300 µl were added to the wells of a 48-well culture plate and allowed to polymerize. Human endothelial cells (3.5×104 per well) were resuspended in EMB2 (Endothelial Cell Basal Medium, Cambrex Bioscience, Walkersville, Md.) medium with 5.0% FBS and allowed to form cords in the presence or absence of CLK-Peptide or the inactive control peptide, CTW (0 to 100 µg/ml). Endothelial morphogenesis and cord formation was monitored with an inverted microscope fitted with a 35 mm camera to document cord formation. As shown in FIG. 6, CLK-peptide dose-dependently inhibited endothelial cord formation while the control peptide had little if any effect, suggesting that the cryptic epitope recognized by CLK-Peptide plays a role in regulating endothelial cell morphogenesis.

Example 8

CLK-Peptide Inhibits M21 Melanoma Tumor Growth in Nude Mice

Figure 7:
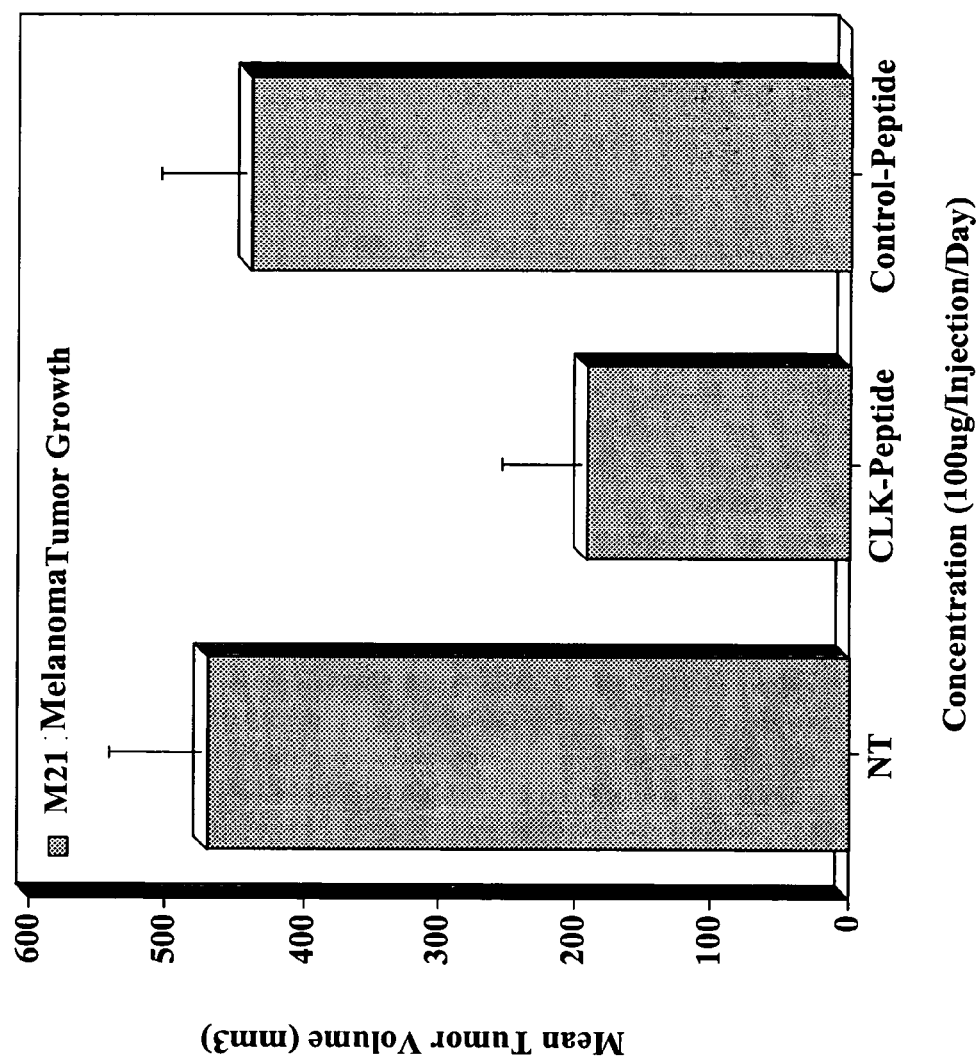
FIG. 7 Effects of CLK-Peptide on M21 Melanoma Tumor Growth in Mice. Nude mice were subcutaneously injected with M21 human melanoma cells. Following injection with CLK-Peptide or the inactive control peptide CTW (250 µg/mouse), tumor growth was monitored by caliper measurement, and tumor volume was estimated using the formula V=L2×W/2, where V=volume, L=length and W=width. The figure shows quantification of tumor growth. Data bars represent the mean tumor volume ±standard error from 5 mice per condition.

The effects of the CLK-Peptide on human M21 melanoma growth in nude mice were assessed in vivo. M21 human melanoma cells ($3 \times 10^6$) were injected subcutaneously into nude mice. Three days later, following establishment of palpable tumors, the mice were treated intraperitoneally with CLK-Peptide or control peptide (250 µg) daily for 24 days. The size of the tumors was monitored by caliper measurement. M21 human melanoma cells formed tumors in untreated mice and in mice treated with control peptide CTW. In contrast, intraperitoneal administration of CLK-Peptide significantly inhibited (P<0.050) M21 human melanoma tumor growth by approximately 60% as compared to controls (FIG. 7), suggesting that the CLK cryptic epitope plays a role in tumor growth.

Example 9

Figure 8:
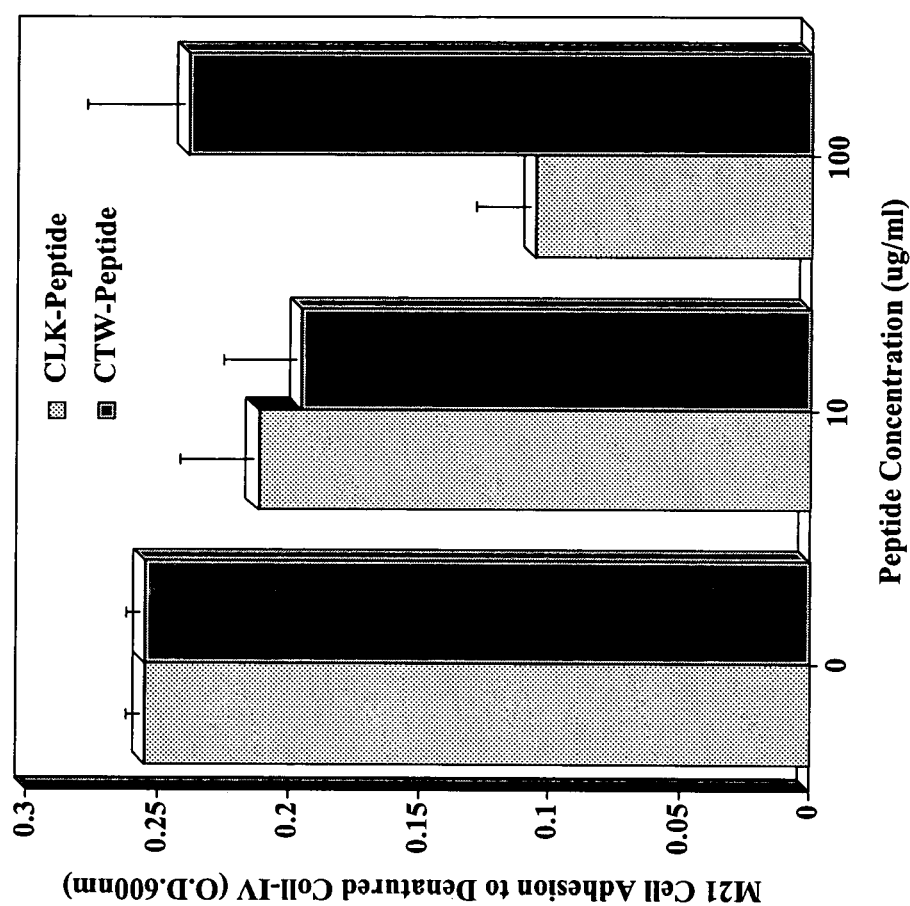
FIG. 8 CLK-Peptide Specifically Inhibits Tumor Cell Adhesion to Denatured Collagen Type-IV. Non-tissue culture treated 48-well plates were coated with denatured collagen type-IV at 10 µg/ml. Human melanoma cells (M21) were allowed to attach to the coated wells in the presence or absence of CLK-Peptide or a inactive control peptide (CTW) at 0-100 µg/ml. Cell adhesion was quantified by measuring the O.D. of eluted dye at 600 nm. Data bars represent the mean O.D.±standard deviation from triplicate wells. Assays were completed 2 to 3 times with similar results.
Figure 9:
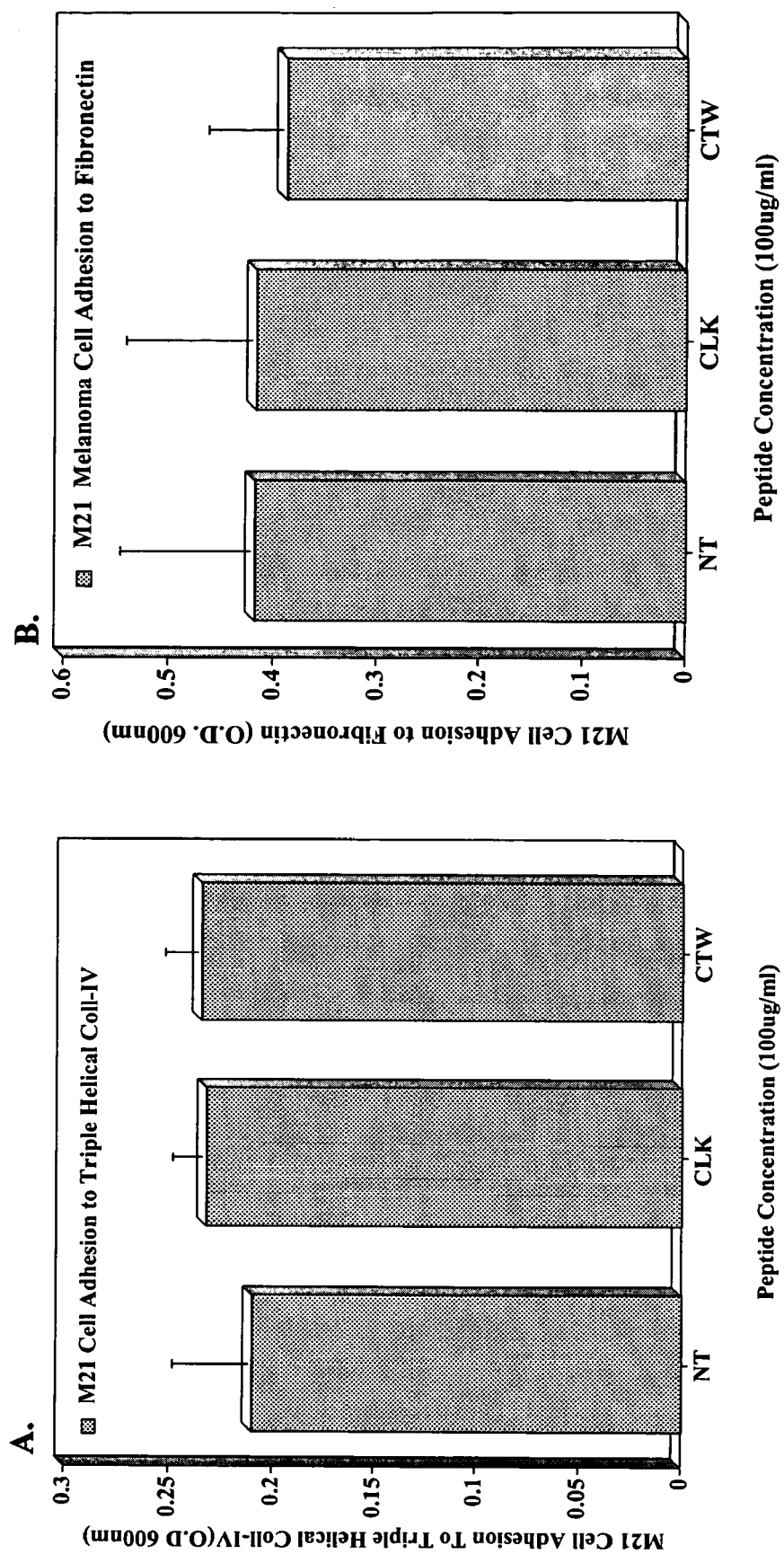
FIG. 9 CLK-Peptide Does not Inhibit Tumor Cell Adhesion to Native Collagen Type-IV. Non-tissue culture treated 48-well plates were coated with native collagen type-IV or fibronectin at 10 µg/ml. Human melanoma cells (M21) were allowed to attach to the coated wells in the presence or absence of CLK-Peptide or control peptide CTW at 0-100 µg/ml. Cell adhesion was quantified by measuring the O.D. of eluted dye at 600 nm. Data bars represent the mean O.D.±standard deviation from triplicate wells. Assays were completed 2 to 3 times with similar results. A. Adhesion to native collagen type-IV. B. Adhesion to Fibronectin.

CLK-Peptide Specifically Inhibits Tumor Cell Adhesion to Denatured Collagen Type-IV Adhesion assays were performed to study the effects of CLK-peptide on tumor cell adhesion in vitro. Microtiter wells were coated with either native collagen type-IV or the control ECM protein fibronectin. Malignant melanoma cells (M21) were allowed to bind to the coated substrates in the presence or absence of CLK peptide or a control peptide, CTW. As shown in FIG. 8, CLK-Peptide dose-dependently inhibited M21 cell attachment to denatured collagen type-IV with maximal inhibition of approximately 65% at 100 µg/ml, while CTW had no effect. Neither CLK-Peptide nor the control peptide had any effect on M21 cell adhesion to native triple helical collagen type-IV or fibronectin (FIGS. 9A and B), suggesting that the cryptic epitope recognized by CLK-Peptide plays a functional role in tumor cell adhesion to denatured collagen type-IV.

Example 10

Figure 10:
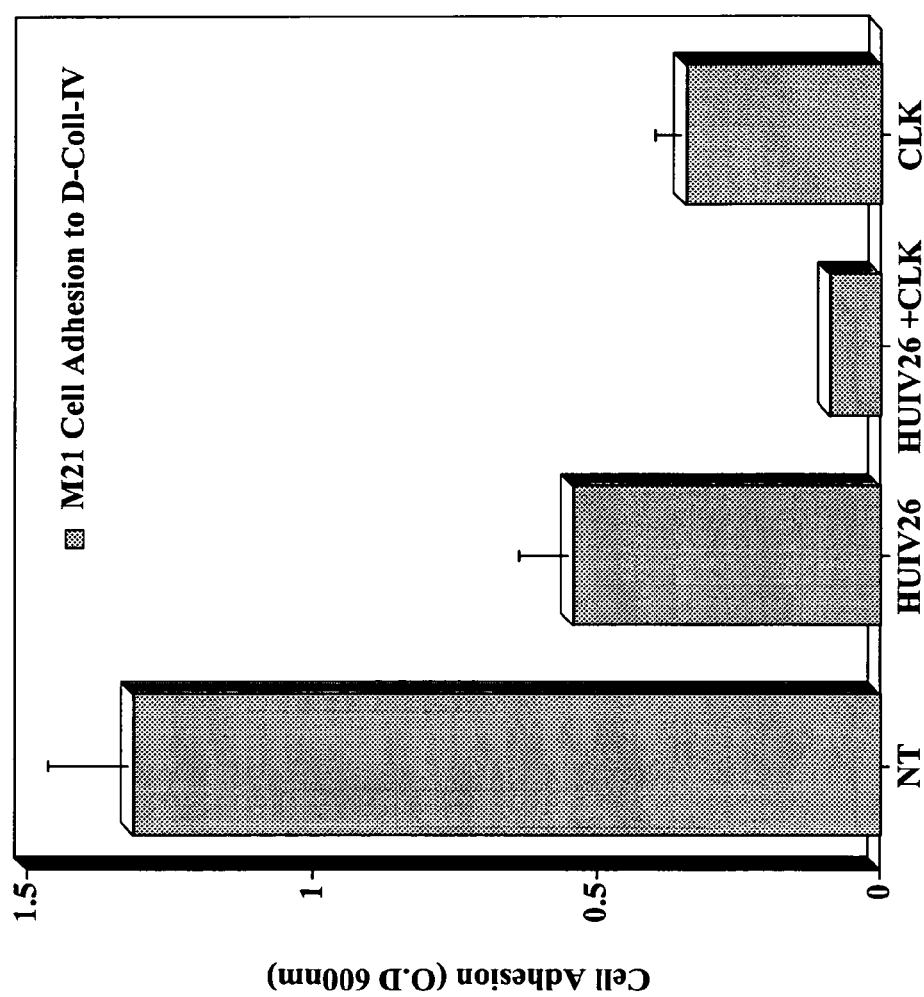
FIG. 10 Effect of mAb HUIV26 in Combination with CLK-Peptide on Adhesion of M21 Cells to Denatured Collagen Type IV. Microtiter wells were coated with denatured collagen type-IV. M21 cells were allowed to bind to the coated substrates in the presence of CLK-peptide, mAb HUIV26, or both. The combination of both CLK-peptide and mAb HUIV26 had a greater effect on adhesion than did either antagonist alone.

Effect of mAb HUIV26 in Combination with CLK-Peptide on Adhesion of M21 Cells to Denatured Collagen Type IV The effects of CLK-peptide, mAb HUIV26, and the combination of both on tumor cell adhesion were examined in vitro. Non-tissue culture treated 48-well microtiter plates were coated overnight at 4° C. with either native or denatured collagen type-IV (5 µg/ml). The plates were then blocked with 1% BSA in PBS for 1 hour at 37° C. Human melanoma (M21) cells at $10^5$ cells/well in adhesion buffer were allowed to attach to the coated wells in the presence of either CLK-peptide (100 μg/ml), or mAb HUIV26 (100 μg/ml), or both together (CLK-peptide 25 μg/ml, mAb HUIV26 100 μg/ml). The cells were washed 2× with PBS, stained with crystal violet and destained with 10% acetic acid. Cell adhesion was quantified by measuring the O.D. of eluted dye at 600 nm. Data bars represent the mean O.D.±standard deviation from triplicate wells. The combinations of both CLK-peptide and mAb HUIV26 had a greater effect on adhesion of M21 cells to denatured collagen type-IV than did either antagonist alone (FIG. 10), whereas neither had any effect on M21 cell adhesion to native collagen type-IV (data not shown).

Example 11

Figure 11:
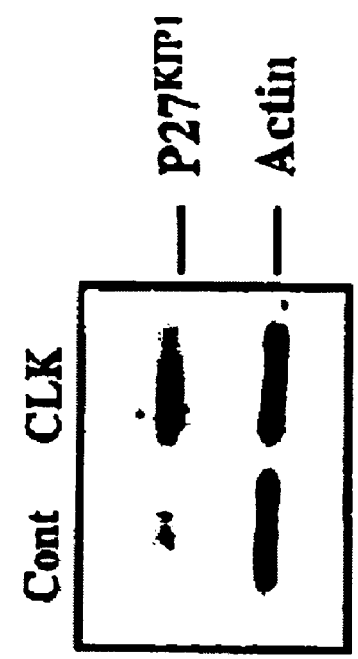
FIG. 11 Inhibition of Cellular Interactions by CLK-Peptide Enhances Expression of P27KIP1. Western Blot analysis of proteins from tumor cells incubated with CLK-peptide showed a significant upregulation of P27KIP1 in comparison to non-tumor controls. A. Treatment of B16F10 melanoma cells. B. Treatment of GL261 glioblastoma cells.
Figure 11:
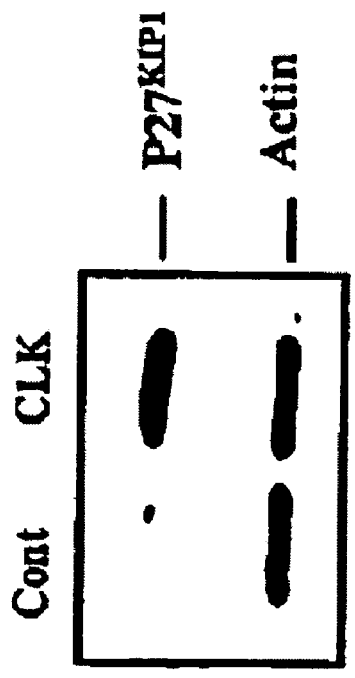

Inhibition of Cellular Interactions by CLK-Peptide Enhances Expression of $P27^{KIP1}$ To determine whether the effect on inhibition of tumor proliferation and invasion in vivo differs in malignant tumors and normal tissue, the effect of CLK-peptide on gene expression was analyzed. Genes that regulate cell cycle control, including Cyclin Dependent Kinase (CDK) inhibitors known to regulate cellular proliferation, were studied. Tumor cells (B16F1O melanoma and GL261 glioblastoma) were resuspended in adhesion buffer in the presence or absence of CLK-peptide or control. Cells were added to culture plates coated with denatured collagen and allowed to incubate for 24 hours. Total cell lysates were prepared and the relative levels of the CDK inhibitor $P_{27}^{KIP1}$ was examined by Western Blot analysis. As shown in FIG. 11, treatment of either B16F10 or GL261 cells with CLK-peptide caused a dramatic upregulation of $P_{27}^{KIP1}$ in comparison to controls, suggesting that CLK-peptide inhibits tumor cell proliferation in part by up-regulating the CDK inhibitor.

Example 12

Figure 12:
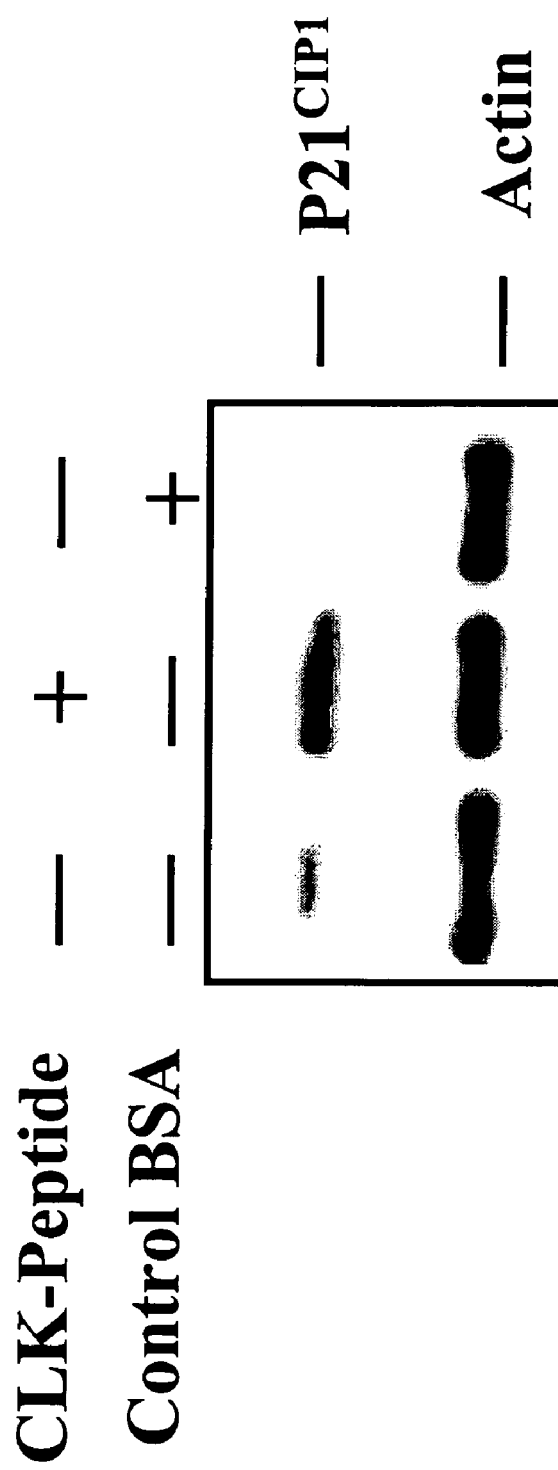
FIG. 12 Inhibition of Cellular Interactions by CLK-Peptide Enhances Expression of P21CIP1 in Human Melanoma (M21) Cells. Non-tissue culture treated 96-well plates were coated with denatured collagen type-IV (10 µg/ml). Human melanoma cells (M21) were allowed to proliferate in the presence or absence of CLK-Peptide or control peptide CTW (100 µg/ml) over a 3-day time course. Cells were then allowed to incubate for 12 hours in 1% serum-containing medium. Expression of P21CIP1 and actin control were evaluated by Western blotting. Tumor cells incubated with CLK-peptide showed a significant upregulation of P21CIP1 in comparison to non-tumor controls.
Figure 13:
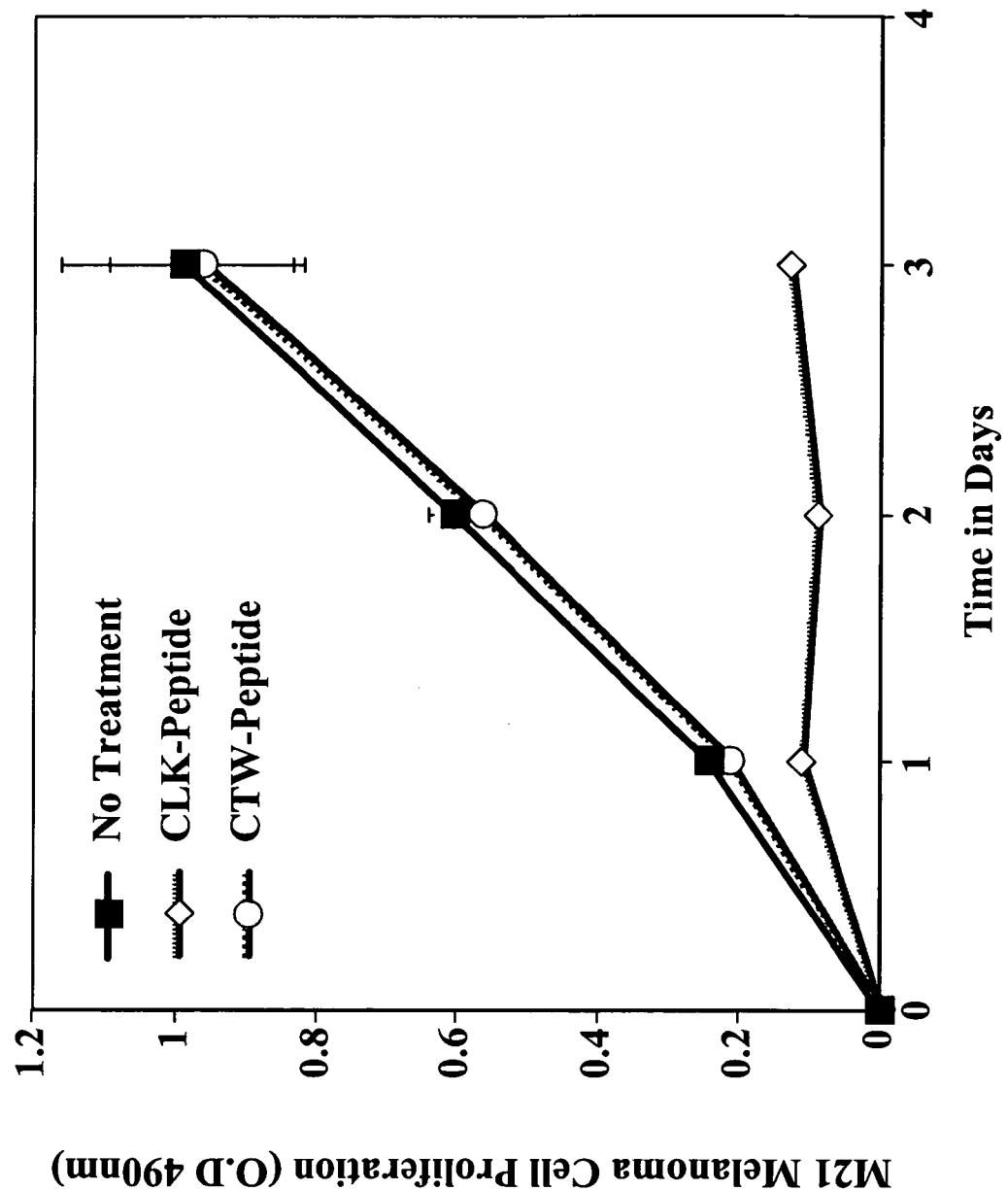
FIG. 13 Effects of CLK-Peptide on Tumor Cell Proliferation. Non-tissue culture treated 96-well plates were coated with denatured collagen type-IV (10 µg/ml). Human melanoma cells (M21) were allowed to proliferate in the presence or absence of CLK-Peptide (open diamonds) or control peptide CTW (100 µg/ml) (open circles) over a 3-day time course. Proliferation was quantified by monitoring mitochondrial dehydrogenase activity at 490 nm. Data bars represent the mean O.D.±standard deviation from triplicate wells.

Inhibition of Cellular Interactions by CLK-Peptide Inhibits Proliferation and Enhances Expression of $P21^{CIP1}$ in Human Melanoma (M21) Cells To examine whether the cryptic epitope recognized by CLK-peptide plays a role in cellular proliferation, in vitro proliferations assays were carried out (FIG. 13). In addition, the effects of CLK-peptide on expression of the CDK inhibitor $p21^{CIP1}$ were examined by Western blotting methods (FIG. 12). Non-tissue culture treated microtiter wells were coated with denatured collagen type-IV. Human M21 melanoma cells were resuspended in 1% RPMI in the presence or absence of CLK or control CTW-peptide (100 μg/ml). Proliferation was monitored by measuring the relative levels of mitochondrial dehydrogenase using a commercially available (WST-I) proliferation kit (Chemicon).

As shown in FIG. 13, CLK-peptide inhibited of M21 melanoma cell proliferation on denatured collagen type-IV by greater than 90% as compared to controls. CLK-Peptide also up-regulated expression of the CDK inhibitor p21CIP1 (FIG. 12). These results suggest that the cryptic epitope defined by CLK-Peptide plays an important functional role in regulating tumor cell proliferation. These data also provide additional support for the concept that the HUIV26 and CLK cryptic epitopes are functionally distinct epitopes and may regulate different cellular processes.

Example 13

Inhibition of Binding of Labeled CLK-Peptide to Denatured Collagen Type-IV by mAbs HUI77 and HUIV26

Figure 14:
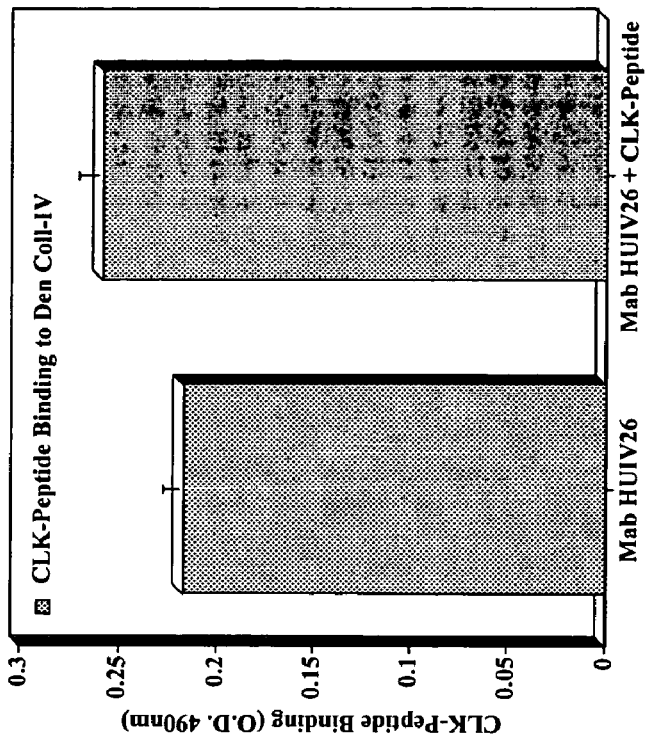
FIG. 14 Inhibition of Binding of Labeled CLK-Peptide to Denatured Collagen Type-IV by mAbs HUI77. To examine the binding specificity of the synthetic CLK-Peptide, the peptide was labeled and solid phase ELISAs were performed. Denatured collagen type-IV (10 µg/ml) was coated on microtiter wells and binding of either HRP-labeled CLK-Peptide or mAbs (mAbs HUI77 or HUIV26) was measured by ELISA at a wavelength of 490 nm. A. Mab HUI77, but not HUIV26, specifically inhibited CLK-Peptide binding to denatured collagen type-IV. B. MAb HUIV26 was allowed to bind the denatured collagen in the presence or absence of CLK-Peptide. As shown, mAb HUIV26 did not block binding of CLK-Peptide.
Figure 14:
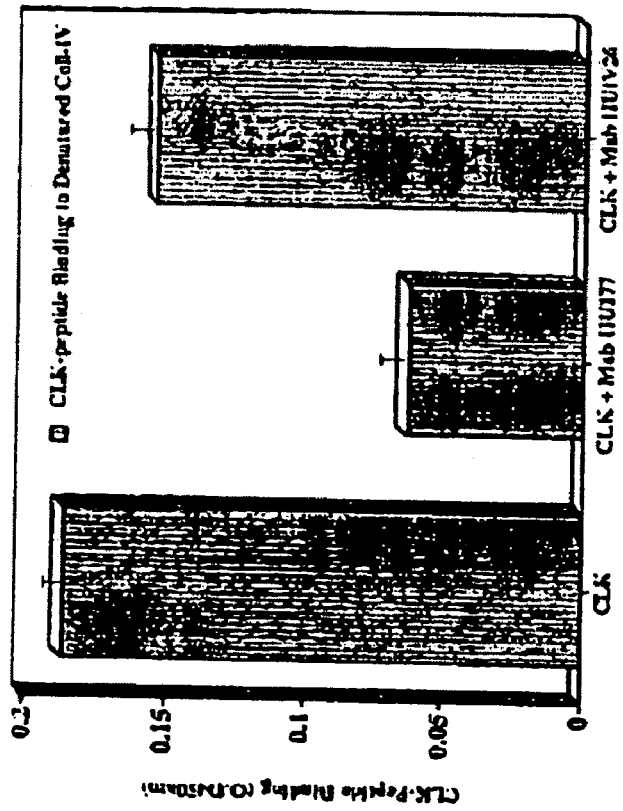

ELISAs were performed to characterize the epitope recognized by the CLK-Peptide and to assess whether it is distinct from that of the HUIV26 cryptic epitope. Denatured collagen type-IV (10 μg/ml) was coated on microtiter wells and binding of HRP-labeled CLK-Peptide, mAb HUI77 or HUIV26 was measured by ELISA at a wavelength of 490 nm. As shown in FIG. 14A, mAb HUI77, but not HUIV26, specifically inhibited CLK-binding to denatured collagen type-IV.

Additionally, competition ELISAs showed that CLK-Peptide does not compete with mAb HUIV26 for binding to denatured collagen type-IV. Microtiter wells were coated with denatured collagen type-IV (1 μg/ml) overnight at 4° C., and the plates blocked with 1% BSA for 1 hour at 37° C. HUIV26 was added at 1 μg/ml and allowed to bind the denatured collagen in the presence or absence of 100 μg/ml CLK-peptide for 2 hours at 37° C. Labeled goat-anti-mouse antibody was added at 1:3000 and incubation was allowed for 1 hour at 37° C. Color solution, then a stopping solution of 4N sulfuric acid, were added and binding was quantified by measuring the O.D. at 490 nm. As shown in FIG. 14B, HUIV26 readily bound to denatured collagen type-IV, and CLK-peptide did not block this binding. Similar results were obtained over a wide range of peptide and antibody concentrations (1 to 100 μg/ml) (data not shown). These data indicate that the CLK-peptide recognizes a cryptic epitope that is distinct from the HUIV26 cryptic collagen site.

Example 14

CLK-Peptide Reacts with a Cryptic Epitope in Collagen Type-IV In Vitro

Figure 15:
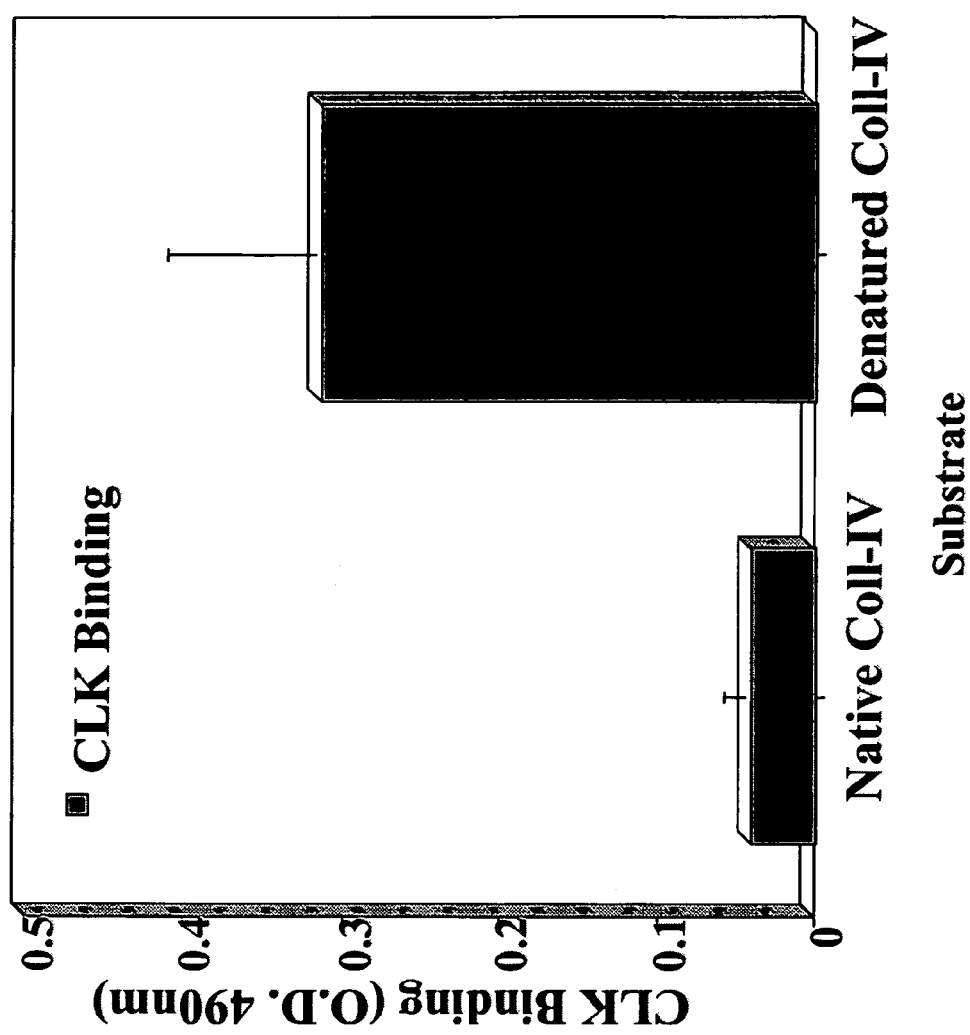
FIG. 15 CLK-Peptide Reacts with a Cryptic Epitope in Collagen Type-IV In Vitro. Reactivity of biotin-labeled CLK-Peptide was assessed by solid phase ELISA. Reactivity was monitored by incubation with HRP-labeled streptavidin. The figure shows quantification of CLK-Peptide binding to (native) triple helical collagen type-IV and denatured collagen type-IV. All data was corrected for nonspecific binding of HRP-labeled streptavidin only. Data bars represent the mean optical density (O.D.)±standard deviation from triplicate wells. Assays were repeated 2 to 3 times with similar results.
Figure 16:
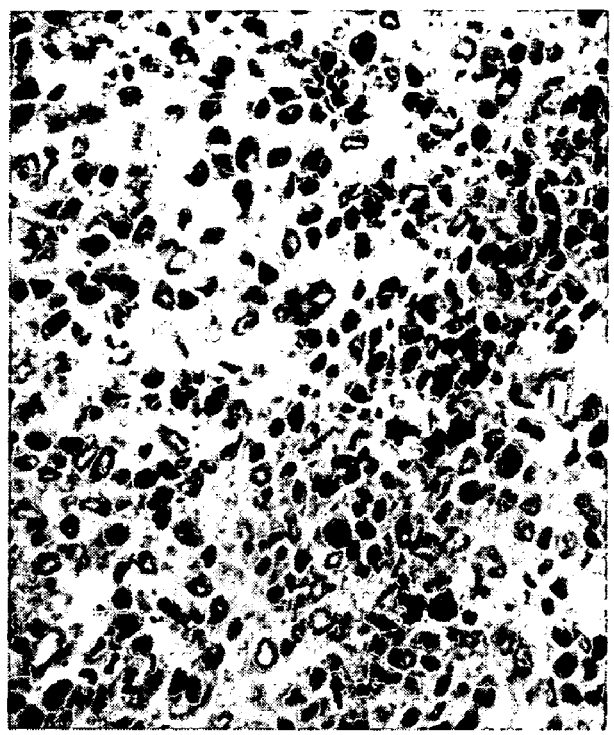
FIG. 16 Expression of the HUI77/CLK Cryptic Epitope in Malignant Tumors in vivo. Frozen sections of human M21 melanoma tumors were analyzed by immunohistochemistry using biotin-labeled CLK-Peptide. The HUI77/CLK cryptic epitope was strongly expressed within M21 melanoma tumors grown in nude mice. A. M21 tumor stained with biotin-labeled CLK-Peptide (100 µg/ml). Brown staining (e.g., at arrows) indicates exposure of the CLK-cryptic epitope. B. M21 tumor stained with control HRP-labeled streptavidin.
Figure 16:
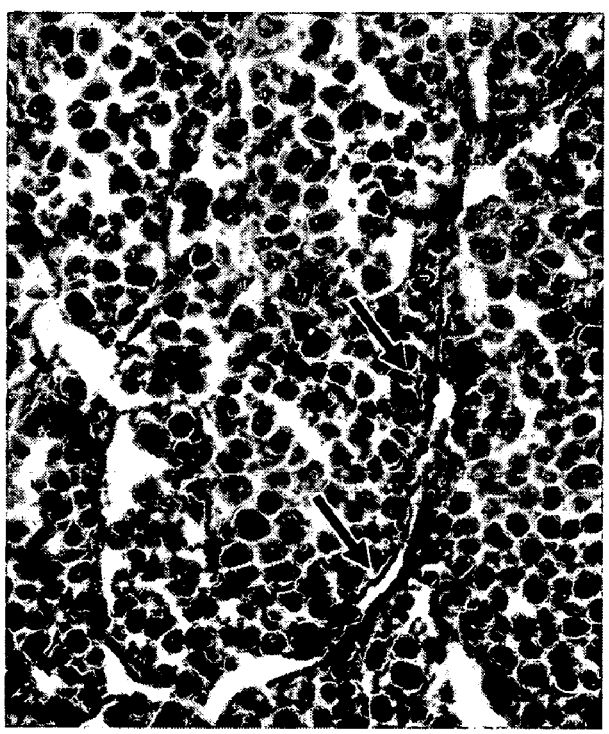
Figure 17:
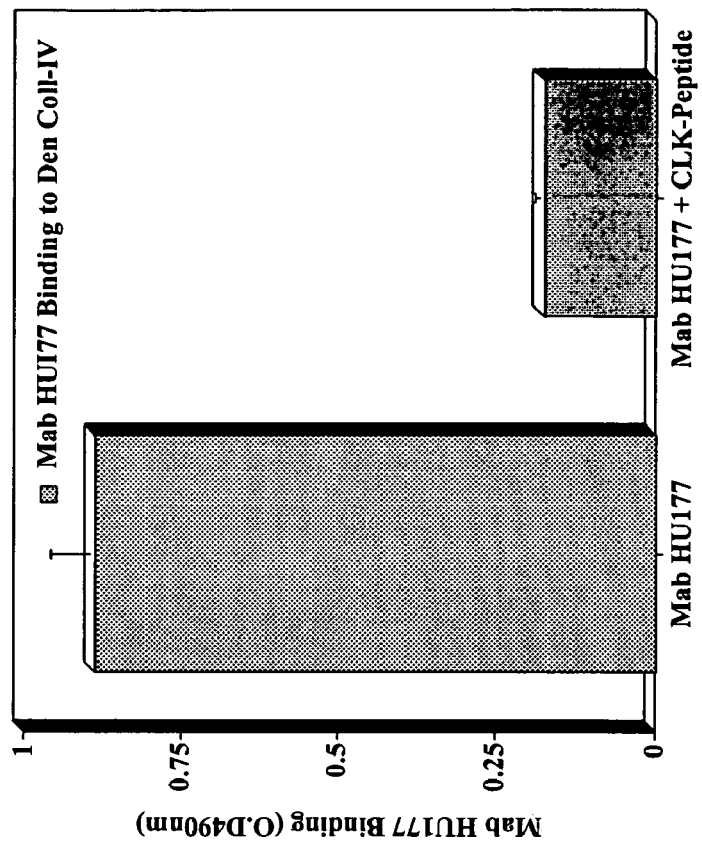
FIG. 17 CLK-Peptide Binds to the HUI77 Cryptic Collagen Epitope. To examine the epitope bound by CLK, competition ELISAs were carried out. Microtiter wells were coated with denatured collagen type-IV (10 µpg/ml), and mAb HUIV26 or HUI77 were allowed to bind the denatured collagen in the presence or absence of CLK-peptide. A. CLK-peptide did not block binding of mAb HUIV26 to denatured collagen. B. CLK-peptide significantly blocked binding of mAb HUI77 to denatured collagen.
Figure 17:
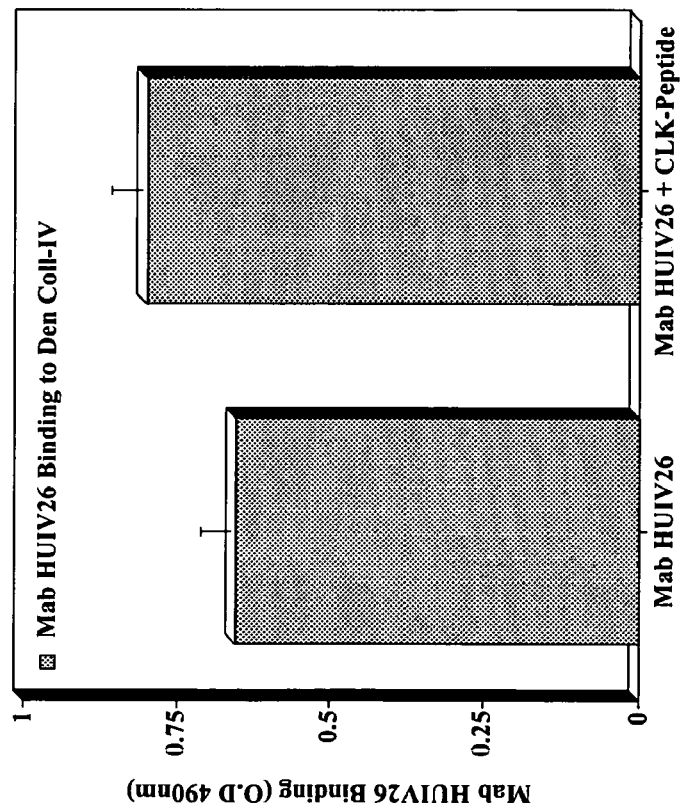

The CLK-peptide was labeled with HRP and used in solid phase ELISA to assess differential binding to either native or denatured collagen type-IV. Microtiter plates were coated with either native or denatured collagen type-IV and HRP-labeled CLK-peptide was allowed to bind. As shown in FIG. 15, CLK-Peptide showed little if any binding to intact triple helical collagen type-IV. In contrast, CLK-Peptide readily bound to denatured collagen type-IV. These findings suggest that the CLK-Peptide selectively binds to a cryptic epitope in denatured collagen type-IV. To determine whether this cryptic epitope was also exposed within the ECM in vivo, biotin-labeled CLK-peptide was used to stain M21 human melanoma tumors growing in nude mice (results shown in FIGS. 16A and B and described in Example 15).

Example 15

Expression of the HUI77/CLK Cryptic Epitope in Malignant Tumors in vivo

Figure 20:
FIG. 20 Exposure of CLK/HUI77 Cryptic Epitope in Malignant Brain Tumor. As described with regard to FIG. 16, exposure of the HUI77/CLK cryptic epitope within collagen type-IV in murine GL261 glioblastoma, was examined. A. CLK/HUI77 B. Control FIG. 21 Effects of CLK-Peptide on Glioblastoma Cell Adhesion to Denatured Collagen Type-IV. Cell adhesion assays using glioblastoma cell line GL261 indicate that CLK-peptide selectively inhibits tumor cell adhesion to denatured collagen type-IV.
Figure 20:

To study the expression of the cryptic collagen sites, exposure of the HUI77/CLK cryptic epitope within collagen type-IV within invasive tumors, including murine GL261 glioblastoma and human melanoma, was examined. Frozen sections of tumors were examined by immunohistochemistry. The HUI77/CLK cryptic epitope was strongly expressed within malignant glioblastoma (FIG. 20) as indicated by staining with Mab HUI77. Furthermore, expression of the HUI77 cryptic epitope was tightly restricted to the tumor ECM while little if any expression was associated with adjacent normal tissue.

In similar studies, biotin-labeled CLK-peptide (100 μg/ml) was used to stain human M21 melanoma tumors (FIGS. 16A and B) grown in nude mice. Following incubation, CLK epitope was detected using HRP-labeled streptavidin.

Example 16

CLK-Peptide Binds to the HUI77 Cryptic Collagen Epitope

ELISAs were performed to examine the binding specificity of CLK-Peptide. Denatured type-IV collagen (10 μg/ml) was coated on microtiter wells and CLK-peptide allowed to bind in the presence or absence of Mab HUI77 or Mab HUIV26 at a 1:1 ratio. HRP-labeled goat anti-mouse secondary antibodies were used to detect murine Mabs HUI77 and HUIV26, directed to distinct cryptic epitope within collagen type-IV, and the O.D. at 490 nm measured.

Example 17

Inhibition of Binding of Labeled CLK-Peptide to Denatured Collagen Type-IV by mAb HUI77

Figure 18:
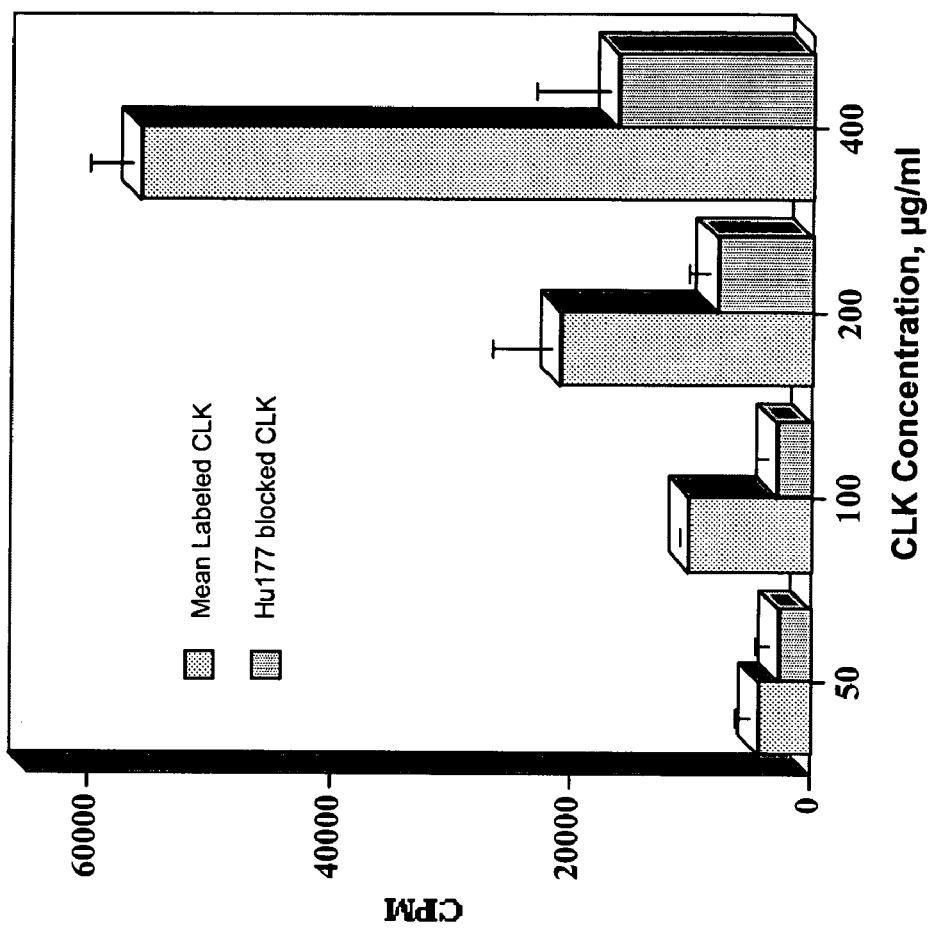
FIG. 18 Inhibition of 99Tc-CLK-Peptide binding by unlabeled HUI77. Binding of 99Tc-CLK-Peptide to denatured collagen type-IV was significantly reduced when the wells were blocked with mAb HUI77.

$^{99}$Tc-CLK-Peptide was used in competitive binding studies to further characterize the CLK epitope. To evaluate the ability of HUI77 to compete with binding to denatured type-IV collagen, type-IV collagen was denatured at 60° C. for 15 minutes at a concentration of 1 μg/ml in PBS. A 96-well polystyrene microtiter plate was filled with 50 μl/well of the denatured type-IV collagen and incubated (covered) overnight at 4° C. The solution was removed by aspiration and the coated wells were washed 3× with 200 μl PBS. The coated wells were then blocked by adding 100 μl of 0.1% BSA for 1 hr at 37° C. Next, 50 μl of HUI77 (1 mg/ml) was added to the collagen-coated wells and incubated for 1 hour at 37° C. 50 μl of $^{99}$Tc-CLK-Peptide (50 to 400 μg/ml) was added to the wells and incubated for an additional 4 hours at 37° C. The supernatant was removed and the wells washed 3× with cold PBS. The supernatant, washes and collagen-coated wells were counted in a gamma counter (1 minute counts in duplicate). As shown in FIG. 18, binding of $^{99}$Tc-CLK-Peptide to denatured collagen type-IV was significantly reduced when the wells were blocked with mAb HUI77.

Figure 19:
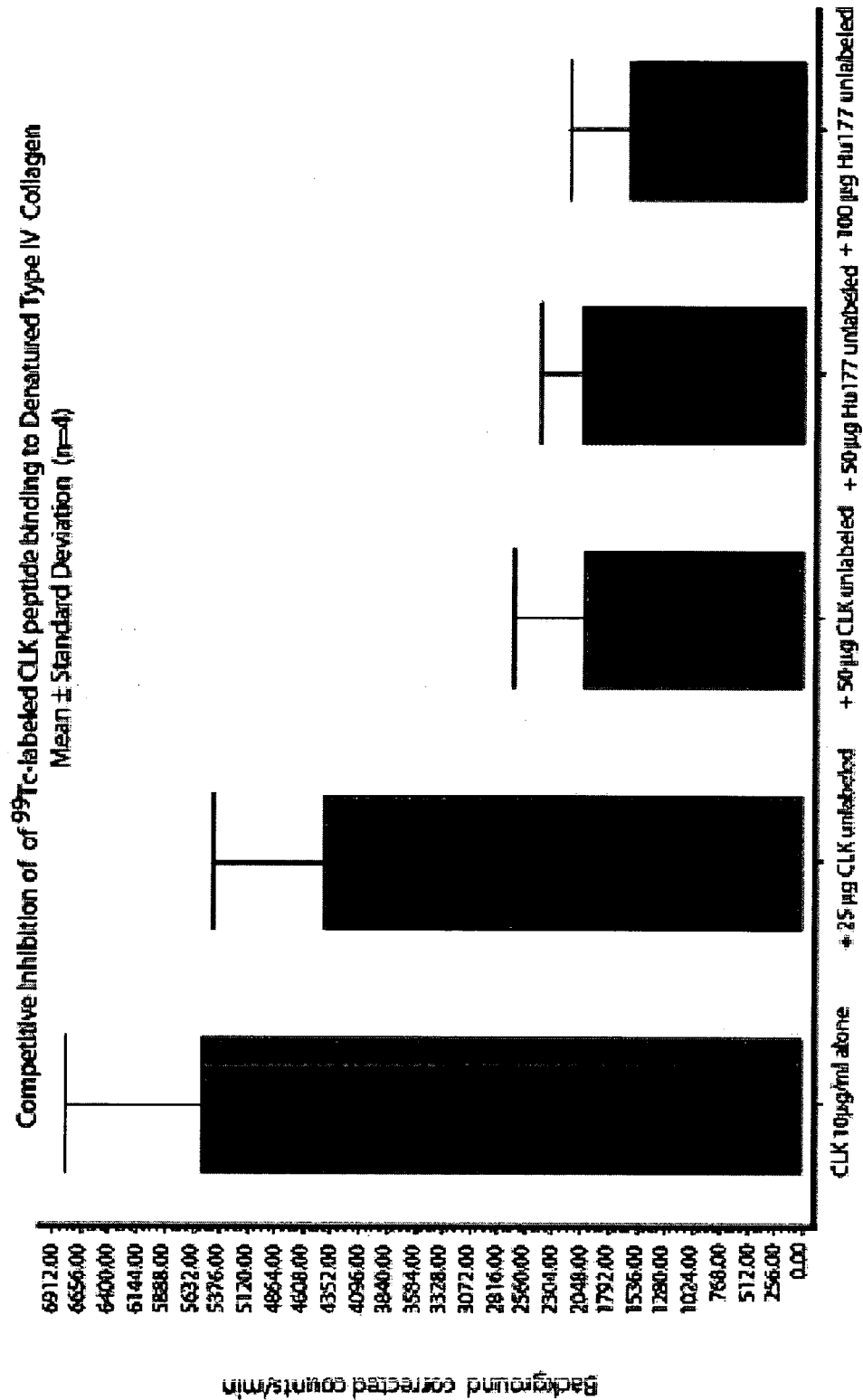
FIG. 19 Inhibition of Binding of Labeled CLK-Peptide to Denatured Collagen Type-IV by mAb HUI77. Denatured collagen type-IV (10 µg/ml) was coated on microtiter wells and binding of 99Tc-labeled CLK-Peptide in the presence or absence of unlabeled CLK-peptide or mAb HUI77 was measured. As shown in the figure, 99Tc-CLK-peptide (10 µg/ml, 50 µl/well) specifically binds to denatured collagen type-IV (first bar from left). Unlabeled CLK-peptide exhibited a dose-dependent inhibition of 99Tc-CLK-peptide binding (second and third bars from left). 99Tc-CLK-peptide was also allowed to bind to denatured collagen type-IV in the presence or absence of Mab HUI77 (fourth and fifth bars from left). Mab HUI77 also inhibited 99Tc-labeled CLK-peptide. These findings provide further evidence that the CLK-peptide binds to a similar if not identical epitope recognized by Mab HUI77.

In addition, denatured collagen type-IV (10 μg/ml) was coated on microtiter wells and binding of $^{99}$Tc-labeled CLK-Peptide in the presence or absence of either unlabeled CLK-peptide or mAb HUI77 was measured using a gamma counter. As shown in FIG. 19, $^{99}$Tc-CLK-peptide (10 μg/ml, 50 μl/well) specifically bound to denatured collagen type-IV (first bar from left). Unlabeled CLK-peptide exhibited a dose-dependent inhibition of $^{99}$Tc-CLK-peptide binding (second and third bars from left). $^{99}$Tc-CLK-peptide was also allowed to bind to denatured collagen type-IV in the presence or absence of Mab HUI77 (fourth and fifth bars from left), which inhibited binding of $^{99}$Tc-labeled CLK-peptide. These findings provide further evidence that the CLK-peptide binds to a similar, if not identical, epitope to that recognized by Mab HUI77.

Example 18

Effects of CLK-Peptide on Glioblastoma Cell Adhesion to Denatured Collagen Type-IV To assess the functional significance of the HUI77/CLK cryptic epitope, cell adhesion assays using a glioblastoma cell line were performed. Microtiter plates were coated with denatured collagen type-IV (10 μg/ml). Glioblastoma (GL261) cells were resuspended in adhesion buffer in the presence or absence of CLK-peptide or a non-specific control (CTW) peptide (50 μg/ml) and the peptides were incubated in the coated wells for 30 minutes. Non-attached cells were removed by washing, and attached cells quantified by staining with crystal violet.

Figure 21:
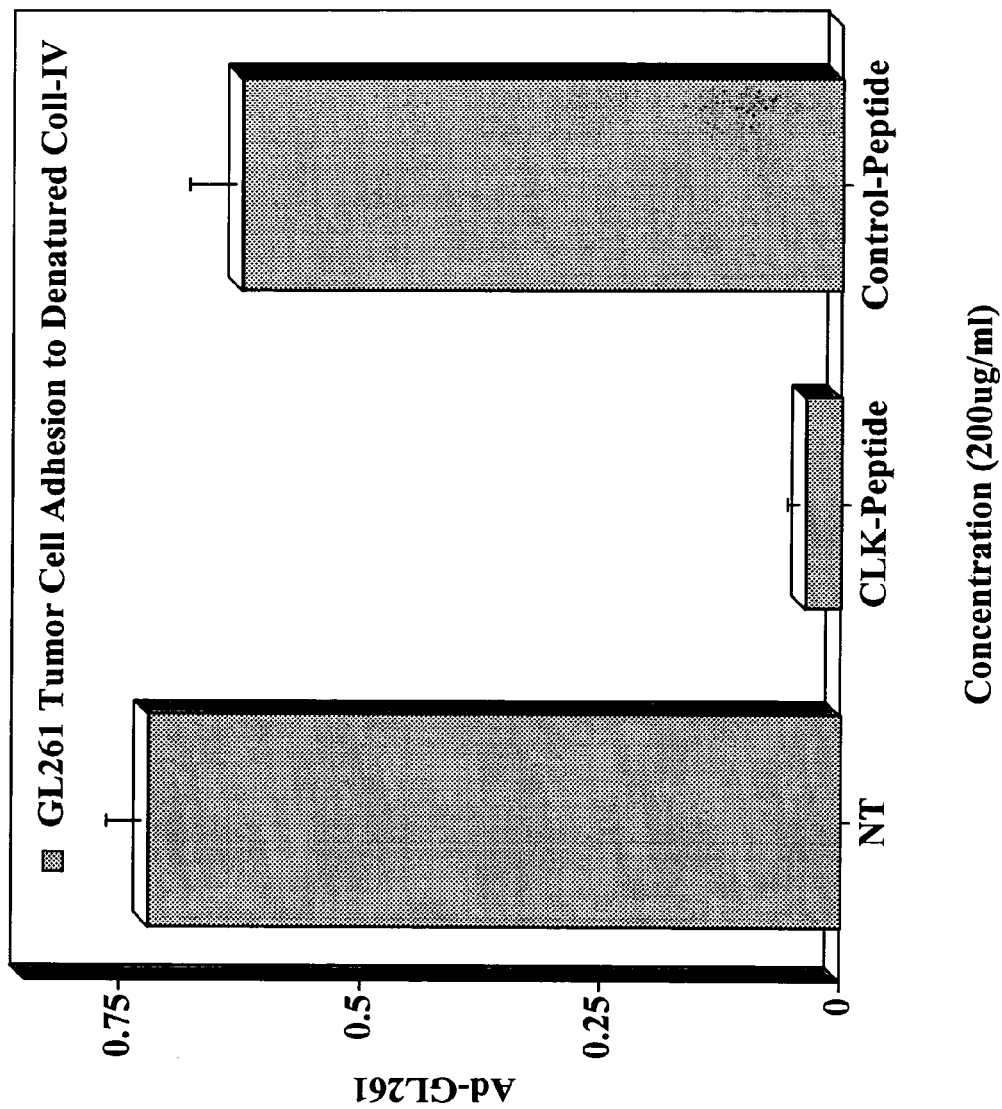

CLK-peptide inhibited glioblastoma cell adhesion to denatured collagen type-IV (90%) while the control peptide had no effect (FIG. 21). In contrast, CLK-peptide had no effect on glioblastoma cell adhesion to native intact collagen type-IV (data not shown), suggesting that CLK-peptide selectively inhibits tumor cell adhesion to denatured collagen type-IV.

Example 19

Effects of CLK-Peptide on Tumor Cell Migration and Proliferation

Figure 22:
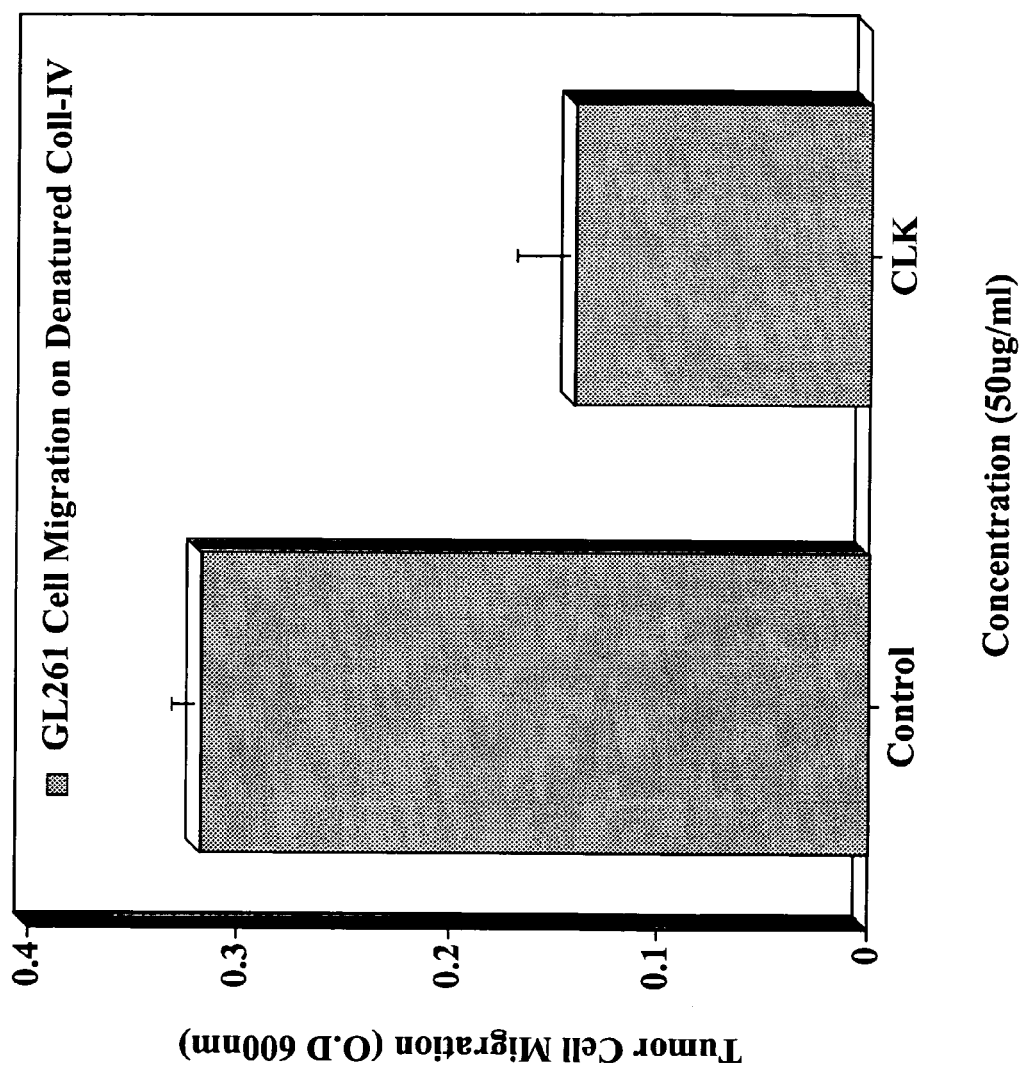
FIG. 22 Effects of CLK-Peptide on Tumor Cell Migration. In cell migration assays, CLK-peptide (50 µg/ml) inhibited GL261 cell migration on denatured collagen type-IV by approximately 50% as compared to control.

The effects of CLK-peptide on invasive tumor cell migration and proliferation in vitro were examined. Membranes from transwell chambers and microtiter wells (in proliferation assays) were coated with denatured collagen type-IV (10 μg/ml). GL261 cells were resuspended in either migration buffer or proliferation buffer in the presence or absence of CLK-peptide or control (50 μg/ml). In the cell migration experiments, GL261 tumor cells were allowed to migrate for 6 hours. Tumor cells that had migrated to the underside of the coated membranes were quantified by staining with crystal violet, and the optical densities of cell-associated dye were measured with a microplate reader at a wavelength of 600 nm. FIG. 22 shows that CLK-peptide (50 μg/ml) inhibited GL261 cell migration on denatured collagen type-IV by approximately 50% as compared to controls.

In further studies, the effects of the CLK-peptide on GL261 tumor cell proliferation was analyzed. GL261 cells were resuspended in proliferation buffer containing 1% serum in the presence or absence of CLK-peptide or control. Tumor cells were allowed to proliferate for 3 days and proliferation was quantified by measuring the relative amount of mitochondrial dehydrogenase using a WST-1 tetrazolium salt cleavage assays kit (Chemicon).

Figure 23:
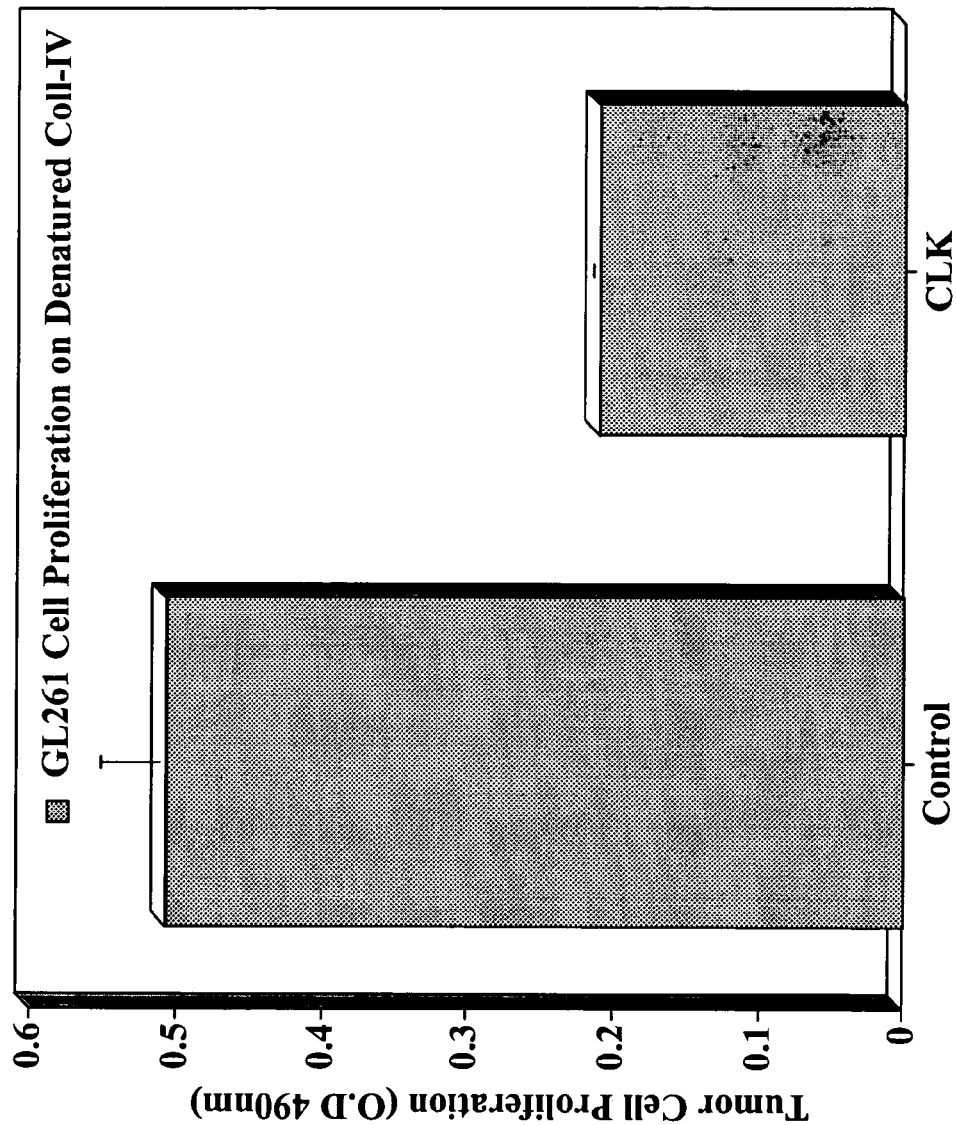
FIG. 23 Effects of CLK-Peptide on Tumor Cell Proliferation. In cell proliferation assays, CLK-peptide (50 µg/ml) inhibited GL261 cell proliferation on denatured collagen type-IV by approximately 50% as compared to control.

FIG. 23 shows that CLK-peptide (100 μg/ml) inhibited GL261 cell proliferation by approximately 50% as compared to controls. These findings suggest that inhibiting tumor cell interactions with the cryptic epitope recognized by the CLK-peptide can inhibit both migration and proliferation, two key cellular processes involved in tumor invasion and progression.

Example 20

CLK-Peptide Enhances the Radiosensitivity of GL216 Glioblastoma

Treatment of GL261 glioblastoma cells with a combination of CLK-peptide and ionizing radiation was found to sensitize the glioblastoma cells to radiation. Microtiter wells were coated with denatured collagen type-IV (10 µg/ml). GL261 cells were resuspended in proliferation buffer containing 1% serum in the presence or absence of a sub-optimal amount of CLK-peptide or control peptide (CTW) (50 µg/ml).

The cells were added to the coated wells and allowed to incubate for 1 hour, then either untreated or irradiated with a single fraction dose of ionizing radiation (5.0 Gy). A $^{60}$Co source (Theratron) was used to deliver a single fraction of 5 Gy. The cells, on a 30 cm$^2$ field, were irradiated from a distance of 80 cm with a gantry angle of 180 degrees on a solid water phantom at 0.5 cm depth.

Tumor cells were allowed to proliferate for 3 days and proliferation was quantified by measuring the relative amount of mitochondrial dehydrogenase using a WST-1 tetrazolium salt cleavage assays kit (Chemicon).

Figure 24:
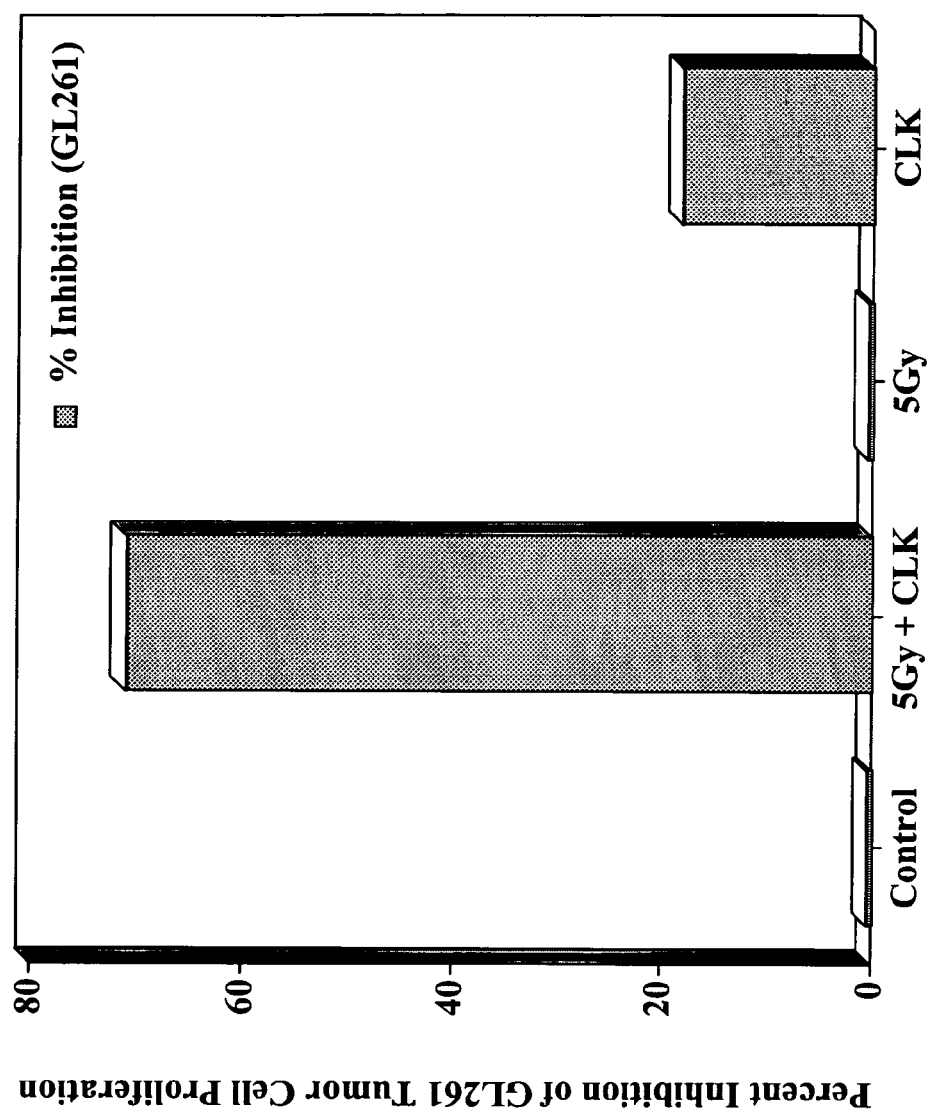
FIG. 24 CLK-Peptide Enhances Radiosensitivity of GL216 Glioblastoma. Percent inhibition of tumor cell proliferation was quantitated in the presence or absence of CLK-Peptide, ionizing radiation, and a combination of the two. Proliferation was dramatically inhibited when CLK-Peptide treatment was combined with ionizing radiation, as compared with inhibition of proliferation by either treatment alone.

As shown in FIG. 24, CLK-Peptide significantly ($P<0.050$) increased the antiproliferative effects of a sub-optimal dose (5.0 Gy) of ionizing radiation on GL261 tumors in vivo by approximately 5-fold as compared to control.

Example 21

Effects of CLK-Peptide on Anti-Tumor Activity of Ionizing Radiation In Vivo

Figure 25:
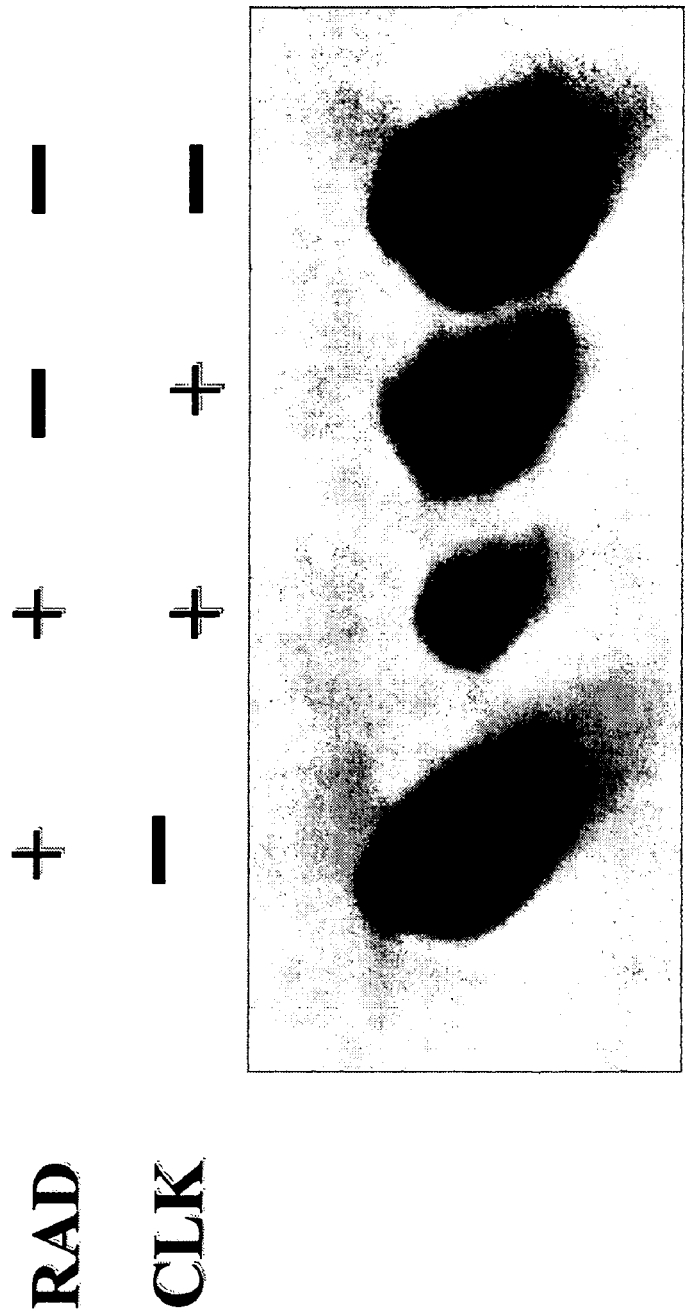
FIG. 25 Effects of CLK-Peptide on Anti-Tumor Activity of Ionizing Radiation In Vivo. Glioblastoma tumors grown on CAMs were treated with either CLK-Peptide, ionizing radiation, both, or left untreated as a control. Their relative sizes after incubation are shown.

The effects of CLK-peptide in combination with ionizing radiation on tumor growth in vivo were assessed. GL261 glioblastoma cells were seeded on the CAMs of 10-day old chick embryos. Twenty-four hours later, the embryos were injected systemically with CLK-peptide (50 µg/embryo). Twenty-four hours after CLK-peptide treatment the embryos were either untreated or irradiated with a single fraction dose of ionizing radiation (5.0 Gy). Photographs showing the relative sizes of embryos given each treatment individually, the combination treatment, and not treated, are shown in FIG. 25. At the end of the 7-day incubation period the tumors (N=6 to 8 per condition) were removed and wet weights determined.

Figure 26:
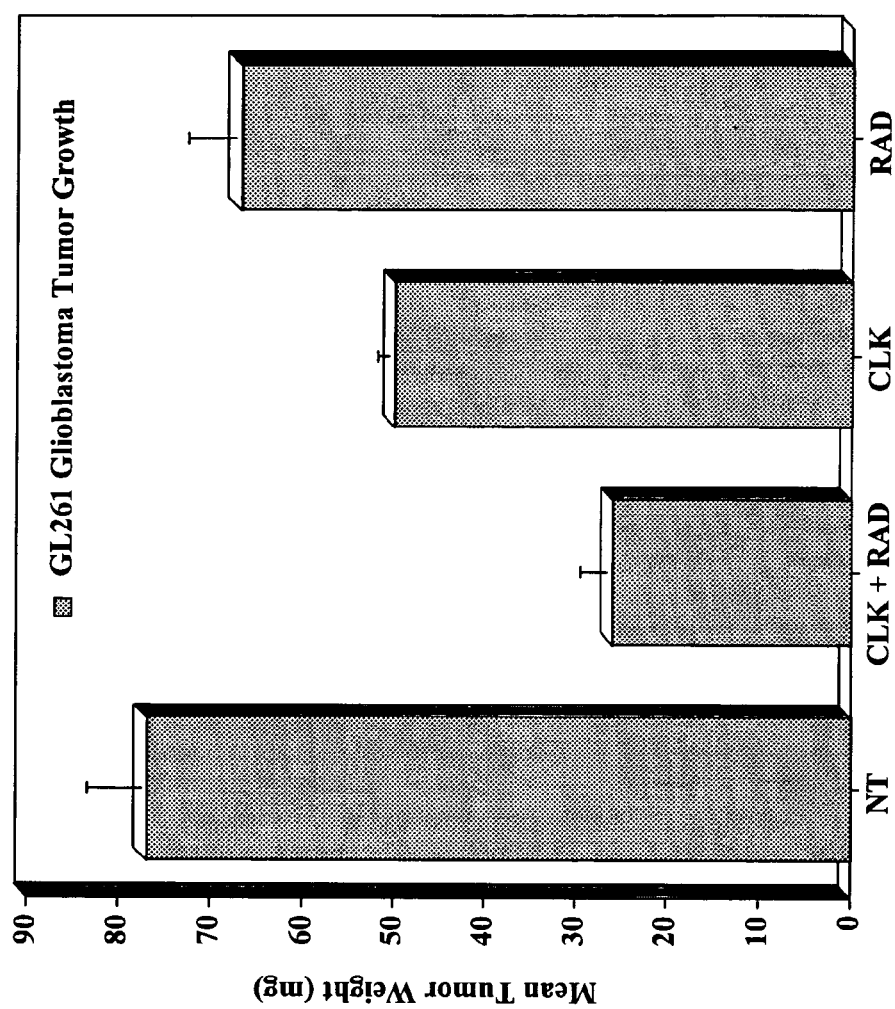
FIG. 26 Quantitation of the Effects of CLK-Peptide on Anti-tumor Activity of Ionizing Radiation in vivo. Glioblastoma tumors grown on CAMs were treated with either CLK-Peptide, ionizing radiation, both, or left untreated as a control. Their relative wet weights following treatment are graphed.

The tumor wet weights, graphed in FIG. 26, indicate that inhibition of tumor growth was greater when the combination therapy was used than when either treatment was administered alone. These results suggest that CLK-Peptide treatment substantially increased the sensitivity of the tumors to radiation treatment.

Example 22

Effects of CLK-Peptide and Ionizing Radiation on Tumor Cell Migration

The effects, of combining CLK-peptide with radiation therapy, on invasive tumor cell migration are examined. GL261 cells are resuspended in migration buffer in the presence or absence of CLK-peptide or control (50 µg/ml). The cells are added to the coated wells and allowed to incubate for 1 hour, and either left untreated or irradiated with a single fraction dose of ionizing radiation (5.0 Gy). The GL261 tumor cells are allowed to migrate for 6 hours. Tumor cells that have migrated to the underside of the coated membranes are quantified by staining with crystal violet, and the optical densities of cell-associated dye are measured with a microplate reader at a wavelength of 600 nm. CLK-peptide in combination with ionizing radiation is found to inhibit GL261 cell migration on denatured collagen type-IV substantially when compared to controls.

Example 23

Effects of CLK-Peptide and Ionizing Radiation on Tumor Cell Adhesion

To test the effect of CLK-peptide in combination with ionizing radiation on tumor growth, in vitro cell adhesion assays using a glioblastoma cell line are performed. Microtiter plates are coated with denatured collagen type-IV (10 µg/ml). Glioblastoma (GL261) cells are resuspended in adhesion buffer in the presence or absence of CLK-peptide or a non-specific control (CTW) peptide (50 µg/ml), and either left untreated or irradiated with a single fraction dose of ionizing radiation (5.0 Gy). The peptides are incubated in the coated wells for 30 minutes Non-attached cells are removed by washing, and attached cells quantified by staining with crystal violet.

A relative increase in adhesion observed in the cells treated with the combination is indicative of an increase in the effectiveness of tumor radiation treatment.

Example 24

Effects of CLK-Peptide and Ionizing Radiation on Tumor Growth in Mice

To test the effect of treating tumors in mice with a combination of CLK-Peptide and radiation, GL261 human glioblastoma cells are injected subcutaneously into the right hind limb ($5\times10^5$ cells in 0.1 ml PBS) of athymic NCR NUM mice and allowed to grow until reaching a diameter of 4-5 mm before treatment. Tumor growth delay (TGD) is determined using time in days for the tumor to grow to 1000 mm$^3$.

In one experiment, CLK-Peptide is used at 150 milligrams per kilogram and given every three days for up to three weeks, using the same schedule with and without a single dose of radiation of 10 Grays (Gy).

In a second experiment, treatment is initiated one week prior to the single dose of radiation. Following the radiation treatment, CLK-Peptide is continued for an additional 21 days, again being administered every third day.

In a third experiment, CLK-Peptide treatment is initiated one week prior to fractionated radiation and continued for up to 21 days, being administered every third day. Fractionated radiation is given in 3 doses of 5 Gray each (3×5 Gy) over three consecutive days. For tumors that receive only fractionated radiation, tumors are size-matched to those receiving CLK-Peptide prior to radiation so that radiation therapy is administered to similarly sized tumors regardless of whether or not they had been pre-treated with CLK-Peptide.

An increase in TGD in the tumors treated with CLK-Peptide and radiation in comparison to tumors treated with CLK-Peptide alone or radiation alone is indicative of suppression and delay in tumor growth achieved by the combined treatments.

All patents and publications which are cited in the body of the instant specification are hereby incorporated by reference in their entirety.

It is also to be appreciated that the foregoing description of the invention has been presented for purposes of illustration and explanation and is not intended to limit the invention to the precise manner of practice herein. It is to be appreciated therefore, that changes may be made by those skilled in the art without departing from the spirit of the invention and that the scope of the invention should be interpreted with respect to the following claims.

The invention claimed is

1. A method of treating a solid tumor in a patient comprising administering to said patient an effective amount of a selective antagonist to denatured collagen type-IV wherein said antagonist is a peptide comprising the core amino acid sequence referenced as SEQ ID NO:1, in combination with radiation therapy.

2. The method of claim 1 wherein said antagonist is a peptide comprising the amino acid sequence referenced as SEQ ID NO:2.

3. The method of claim 1 wherein said solid tumor is selected from the group consisting of: glioblastoma; neuroblastoma; Kaposi's sarcoma; and tumors of the skin, melanoma, lung, pancreas, liver, breast, colon, larynx, pharynx, ovary, uterus, cervix, endometrius, prostate, stomach, intestine, colorectal, head, neck, testicle, lymph node, marrow, bone or joint, kidney, bladder, and sweat gland.

4. The method of claim 1 wherein said radiation therapy comprises ionizing radiation.

5. The method of claim 1 wherein said radiation therapy comprises gamma rays, X-rays, electrons, neutrons, electromagnetic radiation, particulate radiation, electron beams (beta particles), proton beams, neutron beams, alpha particles or negative pi mesons.

6. The method of claim 1 wherein said radiation therapy comprises electromagnetic radiation or particulate radiation.

7. The method of claim 1, wherein a total of at least about: 1 Gy, 5 Gy, 10 Gy, 20 Gy, or 40 Gy of radiation is administered to the patient.

8. A method of treating a solid tumor in a patient comprising administering to said patient an effective amount of a selective antagonist to denatured collagen type-IV wherein said antagonist is a peptide comprising the core amino acid sequence referenced as SEQ ID NO:1, in combination with radiation therapy, wherein the combination of said peptide antagonist and said radiation therapy have a synergistic effect on tumor growth or tumor cell proliferation.

9. A method of treating a solid tumor in a patient comprising administering to said patient an effective amount of a selective antagonist to denatured collagen type-IV wherein said antagonist is a peptide comprising the core amino acid sequence referenced as SEQ ID NO:1, in combination with radiation therapy, wherein treatment with the peptide antagonist increases sensitivity of the tumor to radiation therapy.

* * * * *

UNITED STATES PATENT AND TRADEMARK OFFICE
CERTIFICATE OF CORRECTION

PATENT NO. : 7,662,783 B2 Page 1 of 1
APPLICATION NO. : 11/251442
DATED : February 16, 2010
INVENTOR(S) : Brooks et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 247 days.

Signed and Sealed this

Thirtieth Day of November, 2010

David J. Kappos
*Director of the United States Patent and Trademark Office*